United States Patent [19]

Müller et al.

[11] Patent Number: 5,516,749
[45] Date of Patent: May 14, 1996

[54] HERBICIDAL AND FUNGICIDAL SUBSTITUTED TRIAZOLINONES

[75] Inventors: Klaus-Helmut Müller, Düsseldorf; Klaus König, Odenthal; Kurt Findeisen; Hans-Joachim Santel, both of Leverkusen; Klaus Lürssen; Robert R. Schmidt, both of Bergisch-Gladbach; Stefan Dutzmann, Hilden, all of Germany

[73] Assignee: Bayer Aktiengesellschaft, Leverkusen, Germany

[21] Appl. No.: 180,721

[22] Filed: Jan. 13, 1994

Related U.S. Application Data

[63] Continuation-in-part of Ser. No. 973,488, Nov. 9, 1992, abandoned, which is a continuation-in-part of Ser. No. 852,120, Mar. 16, 1992, abandoned, and Ser. No. 698,253, May 6, 1991, abandoned, which is a continuation of Ser. No. 516,503, May 1, 1990, abandoned.

[30] Foreign Application Priority Data

| May 24, 1989 | [DE] | Germany | 39 169 30.8 |
| Jan. 6, 1990 | [DE] | Germany | 40 002 34.9 |
| Mar. 23, 1991 | [DE] | Germany | 41 096 71.1 |

[51] Int. Cl.⁶ .................. C07D 249/12; A01N 43/653
[52] U.S. Cl. .................. 504/273; 514/384; 548/263.8
[58] Field of Search .................. 504/273; 514/384; 548/263.8

[56] References Cited

U.S. PATENT DOCUMENTS

| 4,743,291 | 10/1988 | Marauetz | 71/92 |
| 5,194,085 | 3/1993 | Lindig et al. | 548/263.8 |

OTHER PUBLICATIONS

Daum et al, "Preparation of Herbicidal and, etc" CA 112: 216935n (1990).

*Primary Examiner*—Patricia L. Morris
*Attorney, Agent, or Firm*—Sprung Horn Kramer & Woods

[57] ABSTRACT

Herbicidal and fungicidal substituted triazolinones of the formula

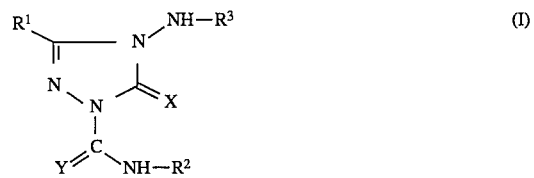

in which $R^1$ represents hydrogen, alkyl alkenyl, alkinyl, halogenoalkyl, halogenoalkenyl, halogenoalkinyl, alkoxyalkyl, cycloalkyl or cycloalkylalkyl, of represents tetrahydrofuranyl or tetrahydrofuranylalkyl, or represents in each case optionally substituted aralkyl or aryl, $R^2$ represents hydrogen, alkyl, alkenyl, alkinyl, halogenoalkyl, halogenoalkenyl, halogenoalkinyl, cyanoalkyl, hydroxyalkyl, alkoxyalkyl, aryloxyalkyl, alkoxycarbonylalkyl, alkoxycarbonylalkenyl, alkylaminoalkyl or dialkylaminoalkyl, or represents in each case optionally substituted cyclocalkyl, cycloalkylalkyl, cycloalkenyl or cycloalkenylalkyl, or represents optionally substituted heterocyclyalkyl, or represents in each case optionally substituted aralkyl, aroyl, aryl, aralkyloxy or aryloxy, or represents alkoxy, alkenyloxy or alkinyloxy, $R^3$ represents alkyl, alkenyl, alkinyl, halogenoalkyl, halogenoalkenyl, halogenoalkinyl, cyanoalkyl, alkoxyalkyl or alkylthioalkyl, or represents in each case optionally substituted cycloalkyl, cycloalkylalkyl, aryl or aralkyl, X represents oxygen or sulphur and Y represents oxygen or sulphur, and new intermediates.

28 Claims, No Drawings

HERBICIDAL AND FUNGICIDAL SUBSTITUTED TRIAZOLINONES

This is a continuation-in-part of application Ser. No. 973,488, filed Nov. 9, 1992, now abandoned, which is a continuation-in-part of application Ser. No. 698,253, filed May 6, 1991, now abandoned, and of application Ser. No. 852,120, filed Mar. 16, 1992, now abandoned; Ser. No. 698,253 is itself a continuation of application Ser. No. 516,503, filed May 1, 1990, now abandoned.

The invention relates to new substituted triazolinones, to several processes for their preparation, and to their use as herbicides and fungicides.

It is known that certain nitrogen heterocycles, such as, for example, 4-amino-3-methyl-6-phenyl-1,2,4-triazin-5-one (cf. DE-OS (German Published Specification) 2,364,474) or 4-amino-1-(N-phenylcarbamoyl)-3-methyltriazolin-5-one (cf. EP-A 294,666), have herbicidal properties.

However, the herbicidal activity of these previously known compounds against problem weeds, as well as their tolerance by important crop plants, is not entirely satisfactory in all fields of application.

Certain substituted triazolinones, such as, for example, 1-(N,N-dimethylcarbamoyl)-3-phenyl-4-amino-1,2,4-triazolin-5-one, are furthermore known (cf, J. Heterocycl. Chem. 17, 1691–1696 [1980]; Org. Mass. Spectrom. 14, 369–378 [1979].

An activity of these previously known triazolinones as herbicides was hitherto unknown.

New substituted triazolinones of the general formula (I)

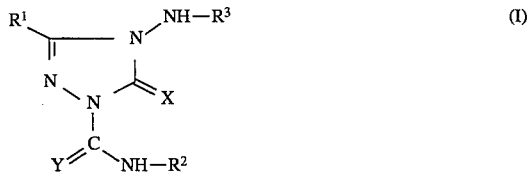

in which

R$^1$ represents hydrogen, alkyl, alkenyl, alkinyl, halogenoalkyl, halogenoalkenyl, halogenoalkinyl, alkoxyalkyl, cycloalkyl or cycloalkylalkyl, or represents tetrahydrofuranyl or tetrahydrofuranylalkyl, or represents in each case optionally substituted aralkyl or aryl, R$^2$ represents hydrogen, alkyl, alkenyl, alkinyl, halogenoalkyl, halogenoalkenyl, halogenoalkinyl, cyanoalkyl, hydroxyalkyl, alkoxyalkyl, aryloxyalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy, R$^3$ represents alkyl, alkenyl, alkinyl, halogenoalkyl, halogenoalkenyl, halogenoalkinyl, cyanoalkyl, alkoxyalkyl or alkylthioalkyl, or represents in each case optionally substituted cycloalkyl, cycloalkylalkyl, aryl or aralkyl, X represents oxygen or sulphur and Y represents oxygen or sulphur, have been found.

Where appropriate, the compounds of the formula (I) can occur as geometric and/or optical isomers or mixtures of isomers of various compositions, depending on the nature of the substituents R$^1$, R$^2$ and R$^3$. The invention claims the pure isomers as well as the mixtures of isomers.

Furthermore, it has been found that the new substituted triazolinones of the general formula (I)

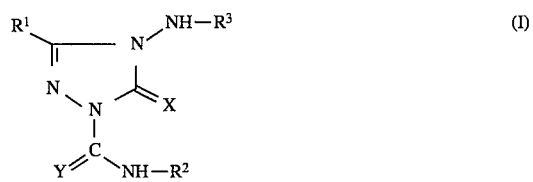

in which

R$^1$ represents hydrogen, alkyl, alkenyl, alkinyl, halogenoalkyl, halogenoalkenyl, halogenoalkinyl, alkoxyalkyl, cycloalkyl or cycloalkylalkyl, or represents tetrahydrofuranyl or tetrahydrofuranylalkyl, or represents in each case optionally substituted aralkyl or aryl, R$^2$ represents hydrogen, alkyl, alkenyl, alkinyl, halogenoalkyl, halogenoalkenyl, halogenoalkinyl, cyanoalkyl, hydroxyalkyl, alkoxyalkyl, aryloxyalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy, R$^3$ represents alkyl, alkenyl, alkinyl, halogenoalkyl, halogenoalkenyl, halogenoalkinyl, cyanoalkyl, alkoxyalkyl or alkylthioalkyl, or represents in each case optionally substituted cycloalkyl, cycloalkylalkyl, aryl or aralkyl, X represents oxygen or sulphur and Y represents oxygen or sulphur, are obtained when (a) 1H-triazolinones of the general formula (II)

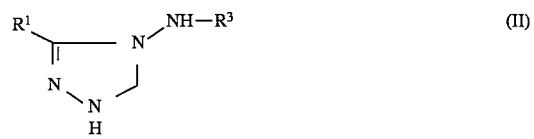

in which
R$^1$, R$^3$ and X have the abovementioned meaning, are reacted with iso(thio)cyanates of the general formula (III)

in which
R$^2$ and Y have the abovementioned meanings, if appropriate in the presence of a diluent and if appropriate in the presence of a reaction auxiliary, or when (b) 1H-triazolinones of the general formula (IV)

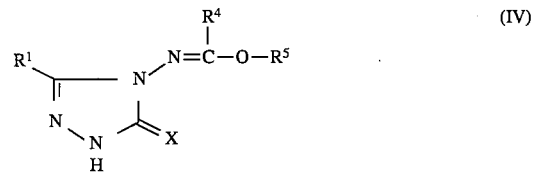

in which
R$^1$ and X have the abovementioned meaning and
R$^4$ and R$^5$ independently of one another represent alkyl, alkenyl, alkinyl, aryl, aralkyl or cycloalkyl, and R$^4$ also represents hydrogen, are reacted with iso(thio)cyanates of the general formula (III)

R²—N=C=Y    (III)

in which

R² and Y have the abovementioned meaning, if appropriate in the presence of a diluent and if appropriate in the presence of a reaction auxiliary and the resulting compounds of the general formula (V)

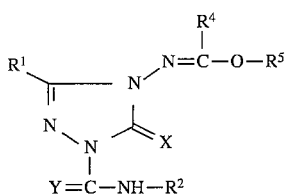    (V)

in which

R¹, R², R⁴, R⁵, X and Y have the abovementioned meanings, are reacted in a second reaction step with a reducing agent of the formula (VI) or (VII)

MBH₄    (VI)

MAlH₄    (VII)

in which

M represents an alkali metal atom, if appropriate in the presence of a diluent, to give the compounds of the general formula (VIII)

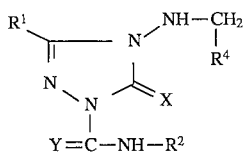    (VIII)

in which

R¹, R², R⁴, X and Y have the abovementioned meaning, or when (c) 1-carbamoyltriazolinones of the general formula (IX)

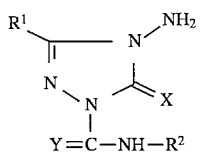    (IX)

in which

R¹, R², X and Y have the abovementioned meaning, are reacted with orthocarboxylic acid esters of the general formula (X)

R⁴—C(OR⁵)₃    (X)

in which

R⁴ and R⁵ have the abovementioned meaning, if appropriate in the presence of a diluent and if appropriate in the presence of a reaction auxiliary, to give compounds of the general formula (V)

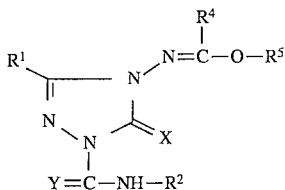    (V)

in which

R¹, R², R⁴, R⁵, X and Y have the abovementioned meaning, and these compounds of the formula (V) are reacted in a second reaction step with a reducing agent of the formula (VI) or (VII)

MBH₄    (VI)

MAlH₄    (VII)

in which

M represents an alkali metal atom, if appropriate in the presence of a diluent, to give the compounds of the general formula (VIII)

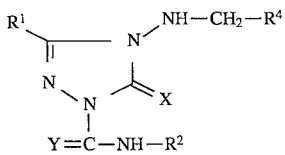    (VIII)

in which

R¹, R², R⁴, X and Y have the abovementioned meanings, or when (d) 1H-triazolinones of the general formula (II)

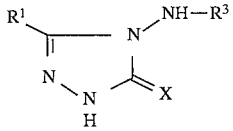    (II)

in which

R¹, R³ and X have the abovementioned meaning, are reacted with (thio)chloroformic acid esters of the general formula (XI)

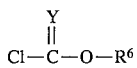    (XI)

in which

R⁷ represents alkyl, aryl or aralkyl and

Y has the abovementioned meaning, if appropriate in the presence of a diluent and if appropriate in the presence of a reaction auxiliary, and the resulting triazolinones of the general formula (XII)

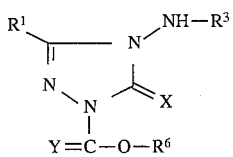    (XII)

in which

R¹, R³, R⁶, X and Y have the abovementioned meaning, are reacted in a subsequent 2nd step with amines of the general formula (XIII)

R²—NH₂    (XIII)

in which
R² has the abovementioned meaning, if appropriate in the presence of a diluent and if appropriate in the presence of a reaction auxiliary to give compounds of the formula (I), or when (e) 1H-triazolinones of the general formula (II)

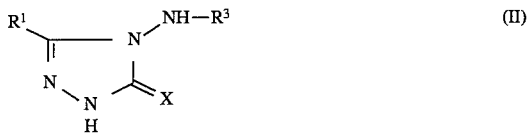

in which
R¹, R³ and X have the abovementioned meanings, are reacted with (thio)urethanes of the general formula (XIV)

in which
R², R⁷ and Y have the abovementioned meaning, if appropriate in the presence of a diluent and if appropriate in the presence of a reaction auxiliary, or when (f) triazolinone-hydrazones of the general formula (XV)

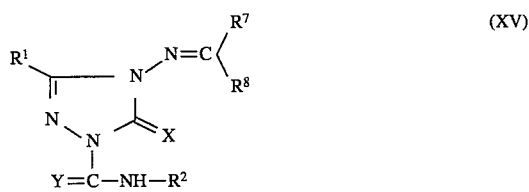

in which
R¹, R², X and Y have the abovementioned meanings and
R⁷ and R⁸ in each case independently of one another represent hydrogen, alkyl, alkenyl, alkinyl, halogenoalkyl, halogenoalkenyl, cycloalkyl, aryl, aralkyl or halogenoalkyl,
are reacted with reducing agents, if appropriate in the presence of catalysts and if appropriate in the presence of diluents.

Finally, it has been found that the new substituted triazolinones of the general formula (I) have excellent herbicidal and fungicidal properties.

Surprisingly, the substituted triazolinones of the general formula (I) according to the invention have a considerably more powerful herbicidal potency against problem weeds than the nitrogen heterocycles which are known from the prior art, such as, for example, 4-amino-3-methyl-6-phenyl-1,2,4-triazin-5-one or 4-amino-1-(N-phenylcarbamoyl)3-methyl-triazolin-5-one, which are similar compounds chemically and from the point of view of their action.

The aromatic radicals in the definitions, such as, for example, aryl, aryloxy or aralkyl, preferably represent phenyl or naphthyl, in particular phenyl. Even when not expressly stated, the aliphatic carbon chains are in each case straight-chain or branched.

The substituent heterocyclylalkyl in R² preferably represents heterocyclylalkyl having 1 to 6 carbon atoms in the straight-chain or branched alkyl moiety and 2 to 9 carbon atoms and 1 to 3 hetero atoms—in particular nitrogen, oxygen and/or sulphur—in the heterocyclyl moiety, it being possible for the heterocyclyl moiety to be monosubstituted or polysubstituted, in particular monosubstituted, disubstituted or trisubstituted by identical or different substituents from the series comprising halogen, cyano, nitro, $C_1$–$C_5$-alkyl, $C_1$–$C_5$-alkoxy, $C_1$–$C_5$-alkylthio, halogeno-$C_1$–$C_5$-alkyl, halogeno-$C_1$–$C_5$-alkoxy, halogeno-$C_1$–$C_5$-alkyl and $C_1$–$C_5$-alkoxycarbonyl. In particular, the heterocyclyl moiety can be substituted by fluorine, chlorine, cyano, nitro, methyl, ethyl, n- or i-propyl, n-, i-, s- or t-butyl, methoxy, ethoxy, methylthio, trifluoromethyl, trifluoromethoxy or trifluoromethylthio. The substituent heterocyclylalkyl in R² particularly preferably represents heterocyclylmethyl, heterocyclylpropyl or heterocyclylethyl, each of which is optionally monosubstituted to trisubstituted in the heterocyclyl moiety by identical or different substituents, and suitable heterocycles in each case being:

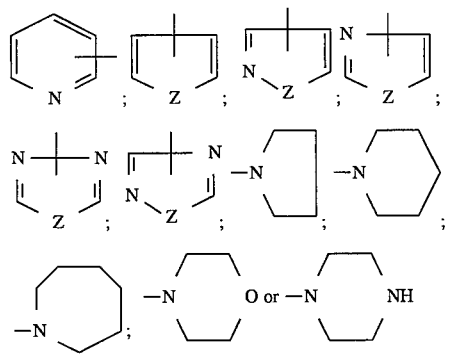

Z in each case representing oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio.

Formula (I) provides a general definition of the substituted triazolinones according to the invention. Preferred compounds of the formula (I) are those in which:

R¹ represents hydrogen, or represents in each case a straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms or alkoxyalkyl having 1 to 6 carbon atoms in the individual alkyl moieties, or represents cycloalkyl or cycloalkylalkyl, each of which has 3 to 7 carbon atoms in the cycloalkyl moiety and if appropriate 1 to 6 carbon atoms in the straight-chain or branched alkyl moiety, or represents tetrahydrofuranyl, or represents tetrahydrofuranylalkyl, if appropriate having 1 to 4 carbon atoms in the straight-chain or branched alkyl moiety, or represents aralkyl or aryl, each of which has 6 to 10 carbon atoms in the aryl moiety and where appropriate 1 to 6 carbon atoms in the straight-chain or branched alkyl moiety and each of which is optionally monosubstituted or polysubstituted by identical or different substituents, suitable aryl substituents in each case being: halogen, cyano, nitro and in each case straight-chain or branched alkyl, alkoxy, alkylthio, halogenoalkyl, halogenoalkoxy or halogenoalkylthio, each of which has 1 to 4 carbon atoms and where appropriate 1 to 9 identical or different halogen atoms, R² represents hydrogen, or represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, each of which has 2 to 8 carbon atoms and 1 to 15, or 13, identical or different halogen atoms, cyanoalkyl having 1 to 8 carbon atoms or hydroxyalkyl having 1 to 8 carbon atoms and 1 to 6 hydroxyl groups, or represents phenoxyalkyl having 1 to 4 carbon atoms in the alkyl moiety, or alkoxyalkyl, alkoxycarbonylalkyl or alkoxycarbonylalkenyl, each of which has up to 6 carbon atoms in the individual alkyl or alkenyl moieties, or alkylaminoalkyl or dialkylaminoalkyl, each of which has 1 to 6 carbon atoms in the individual alkyl moieties, or represents cycloalkyl, cycloalkylalkyl, cycloalkenyl or cycloalkenylalkyl, each of which has 3 to 8 carbon atoms in the cycloalkyl or cycloalkenyl moiety and where appropriate 1 to 6 carbon atoms in the alkyl moiety and each of which is optionally monosubstituted or polysubstituted by identical or different substituents in the heterocyclyl moiety, suitable substituents in each case being: halogen, cyano and in each case straight-chain or branched alkyl or halogenoalkyl, each of which has 1 to 4 carbon atoms and if appropriate 1 to 9 identical or different halogen atoms, or straight-chain or branched halogenoalkyl having up to 4 carbon atoms and 1 to 5 identical or different halogen atoms, or alkanediyl, or alkenediyl, each of which has up to 4 carbon atoms and each of which is double-linked; $R^2$ furthermore represents heterocyclylalkyl which has 1 to 6 carbon atoms in the straight-chain or branched alkyl moiety and 2 to 9 carbon atoms and 1 to 3 hereto atoms—in particular nitrogen, oxygen and/or sulphur—in the heterocyclyl moiety and which is optionally monosubstituted or polysubstituted by identical or different substituents in the heterocyclyl moiety, suitable substituents in each case being: halogen, cyano, nitro and in each case straight-chain or branched alkyl, alkoxy, alkylthio, halogenoalkyl, halogenoalkoxy, halogenoalkylthio or alkoxycarbonyl, each of which has 1 to 5 carbon atoms and where appropriate 1 to 9 identical or different halogen atoms; $R^2$ furthermore represents in each case straight-chain or branched alkoxy having 1 to 8 carbon atoms, alkenyloxy having 2 to 8 carbon atoms or alkinyloxy having 2 to 8 carbon atoms, and finally represents aralkyl, aroyl, aryl, aralkyloxy or aryloxy, each of which has 6 to 10 carbon atoms in the aryl moiety and where appropriate 1 to 8 carbon atoms in the straight-chain or branched alkyl moiety and each of which is optionally monosubstituted or polysubstituted by identical or different substituents, suitable alkyl substituents, where appropriate, being halogen and cyano and suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which has 1 to 6 carbon atoms in the alkyl moiety and where appropriate 1 to 9 identical or different halogen atoms, or cycloalkyl having 3 to 6 carbon atoms, and phenoxy; or $R^2$ represents benzyl having an —O—CH$_2$—O— group which is fused to the phenyl moiety, $R^3$ represents $C_2$–$C_8$-alkyl, $C_2$–$C_8$-alkenyl, $C_3$–$C_6$-cycloalkyl or phenyl-$C_1$–$C_4$-alkyl, X represents oxygen or sulphur and Y represents oxygen or sulphur.

Particularly preferred compounds of the formula (I) are those in which $R^1$ represents hydrogen, methyl, ethyl, n- or i-propyl, n-, i-, s- or t-butyl, n- or i-pentyl or n- or i-hexyl, or represents allyl, propargyl, straight-chain or branched halogenoalkyl having 1 to 4 carbon atoms and 1 to 9 identical or different halogen atoms, in particular fluorine, chlorine or bromine, or represents methoxymethyl, ethoxymethyl, propoxymethyl, cyclopentyl, cyclohexyl, cyclopropyl, cyclopropylmethyl, cyclohexylmethyl or cyclohexylethyl, or represents tetrahydrofuranyl, or represents tetrahydrofuranylmethyl, or represents benzyl or phenyl, each of which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^2$ represents hydrogen, methyl, ethyl, n- or i-propyl, n-, i-, s- or t-butyl, in each case straight-chain or branched pentyl, hexyl, heptyl, octyl, nonyl, decyl or dodecyl, or represents allyl, in each case straight-chain or branched butenyl, pentenyl or hexenyl, propargyl, in each case straight-chain or branched butinyl, pentinyl or hexinyl, or represents straight-chain or branched halogenoalkyl having 1 to 8 carbon atoms and 1 to 9 identical or different halogen atoms, in particular fluorine, chlorine or bromine, or represents in each case straight-chain or branched halogenoalkenyl or halogenoalkinyl, each of which has 3 to 8 carbon atoms and 1 to 3 halogen atoms, in particular fluorine or chlorine, or represents in each case straight-chain or branched cyanoalkyl having 1 to 6 carbon atoms in the alkyl moiety, or hydroxyalkyl having 1 to 6 carbon atoms and 1 to 3 hydroxyl groups, or alkoxyalkyl, alkoxycarbonylalkyl or alkoxycarbonylalkenyl, alkylaminoalkyl or dialkylaminoalkyl, each of which has up to 4 carbon atoms in the individual alkyl or alkenyl moieties, or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, each of which is optionally monosubstituted to trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or dichloroallyl;

$R^2$ furthermore represents heterocyclylmethyl, heterocyclylpropyl or heterocyclylethyl, each of which is optionally monosubstituted to trisubstituted in the heterocyclyl moiety by identical or different substituents, suitable heterocycles in each case being:

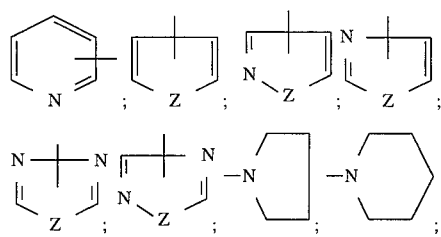

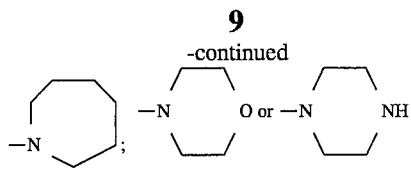

Z in each case representing oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio;

$R^2$ furthermore represents in each case straight-chain or branched alkoxy having 1 to 6 carbon atoms, alkenyloxy having 3 to 6 carbon atoms or alkinyloxy having 3 to 6 carbon atoms, or represents, where appropriate straight-chain or branched, benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, $R^3$ represents methyl, ethyl, n-propyl, n-butyl, i-propyl, i-butyl or cyclopropyl, X represents oxygen or sulphur and Y represents oxygen or sulphur.

Very particularly preferred compounds of the formula (I) are those in which $R^1$ represents hydrogen, methyl, ethyl, n- or i-propyl, methoxymethyl, ethoxymethyl or propoxymethyl, $R^2$ represents hydrogen, or represents methyl, ethyl, n- or i-propyl, n-, i-, s- or t-butyl, allyl, propargyl, in each case straight-chain or branched pentyl, hexyl, heptyl, octyl, butenyl, pentenyl, hexenyl, butinyl, pentinyl or hexinyl, each of which is optionally monosubstituted to trisubstituted by fluorine and/or chlorine; furthermore represents cyclopropyl, cyclopentyl, cyclohexyl, cyclohexenyl, cyclopropylmethyl, cyclopropylethyl, cyclohexylmethyl, cyclohexylethyl or cycloheptyl, each of which is optionally monosubstituted to trisubstituted by identical or different substituents from the series comprising fluorine, chlorine, methyl, ethyl and/or cyano, and finally represents benzyl, phenylethyl or phenyl, $R^3$ represents methyl, ethyl, n-propyl or isopropyl, X represents oxygen or sulphur and Y represents oxygen or sulphur.

In addition to the compounds mentioned in the Preparation Examples, the following substituted triazolinones of the general formula (I) may be mentioned individually:

| $R^1$ | $R^2$ | $R^3$ | X | Y |
|---|---|---|---|---|
| CH₃ | cyclohexyl (H) with CH₃ | CH₃ | O | O |
| CH₃ | H₃C—CH—CF₂ (cyclopropyl with CH₃ and two F) | CH₃ | O | O |
| CH₃ | cyclohexenyl with CH₃ | CH₃ | O | O |
| CH₃ | —C(CH₃)₃ | CH₃ | O | S |
| CH₃ | —C(CH₃)₃ | CH₃ | S | S |
| CH₃ | cyclohexyl (H) | CH₃ | S | S |
| CH₃ | N≡C—cyclohexyl (H) | CH₃ | O | O |

-continued
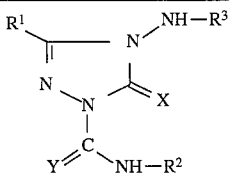 (I)
| R¹ | R² | R³ | X | Y |
|---|---|---|---|---|
| C₂H₅ | —C(CH₃)₃ | CH₃ | O | O |
| C₂H₅ | —C(CH₃)₃ | CH₃ | O | S |
| C₂H₅ | —C(CH₃)₃ | CH₃ | S | O |
| C₂H₅ | 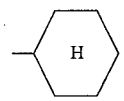 | CH₃ | O | S |
| C₂H₅ | 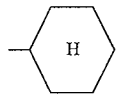 | CH₃ | S | O |
| C₂H₅ | 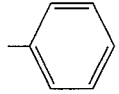 | C₂H₅ | O | O |
| C₂H₅ | 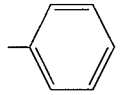 | C₂H₅ | O | S |
| C₂H₅ |  | C₂H₅ | S | O |
| C₂H₅ | 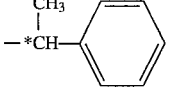<br>S-Configuration | CH₃ | O | O |
| H | —C(CH₃)₃ | C₃H₇-i | O | O |
| H | 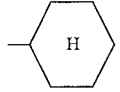 | CH₃ | O | O |
| H | 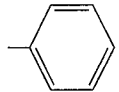 | C₃H₇ | O | O |
| H | —C(CH₃)₃ | CH₃ | O | S |
| H | —C(CH₃)₃ | CH₃ | S | O |
| H | 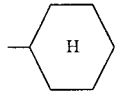 | CH₃ | O | S |
| H | 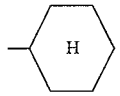 | CH₃ | S | O |
| CH₃ | 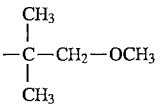 | CH₃ | O | O |

-continued
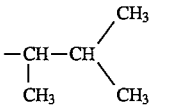
(I)
| R¹ | R² | R³ | X | Y |
|---|---|---|---|---|
| CH₃ | 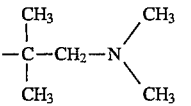 | CH₃ | O | O |
| CH₃ | 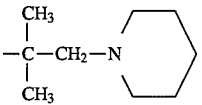 | CH₃ | O | O |
| CH₃ | 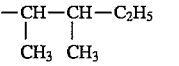 | CH₃ | O | O |
| CH₃ | —CH—CH—C₂H₅<br>　\|　　\|<br>　CH₃　CH₃ | CH₃ | O | O |
| CH₃ | 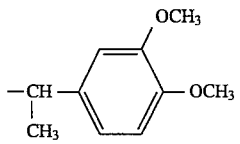 | CH₃ | O | O |
| CH₃ | 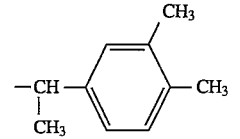 | CH₃ | O | O |
| CH₃ | 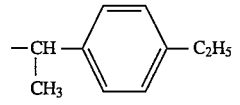 | CH₃ | O | O |
| CH₃ | 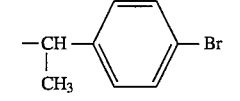 | CH₃ | O | O |
| CH₃ | 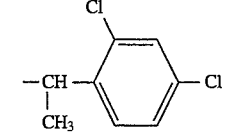 | C₂H₅ | O | O |
| CH₃ | 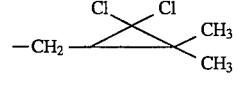 | CH₃ | O | O |
| CH₃ | 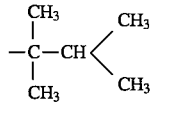 | CH₃ | O | O |
| CH₃ | 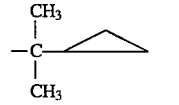 | C₂H₅ | O | O |

-continued $$\text{(I)}$$

| R¹ | R² | R³ | X | Y |
|---|---|---|---|---|
| CH₃ | -C(CH₃)₂-CH(CH₃)-C₂H₅ | CH₃ | O | O |
| CH₃ | -C(CH₃)₂-CH₂-CH(CH₃)₂ | CH₃ | O | O |
| CH₃ | -C(CH₃)₂-C(CH₃)₂-CH₃ | CH₃ | O | O |
| CH₃ | -C(CH₃)₂-CH₂-C₆H₅ | CH₃ | O | O |
| CH₃ | -CH(CH₃)-COOC₂H₅ | CH₃ | O | O |
| CH₃ | -CH(CH₃)-CH₂-CH₂-CH(CH₃)-(CH₂)₂-CH₃ | CH₃ | O | O |
| CH₃ | -CH[(CH₂)₂-CH₃]₂ | CH₃ | O | O |
| CH₃ | -C(C₂H₅)₂-CH₃ | CH₃ | O | O |
| CH₃ | 2-chlorocyclohexyl | CH₃ | O | O |
| CH₃ | -CH₂-CH₂-(3-CF₃-C₆H₄) | CH₃ | O | O |
| CH₃ | -CH₂-CH₂-(4-Br-C₆H₄) | C₂H₅ | O | O |
| CH₃ | -CH₂-CH₂-(2,4-(OCH₃)₂-C₆H₃) | C₂H₅ | O | O |

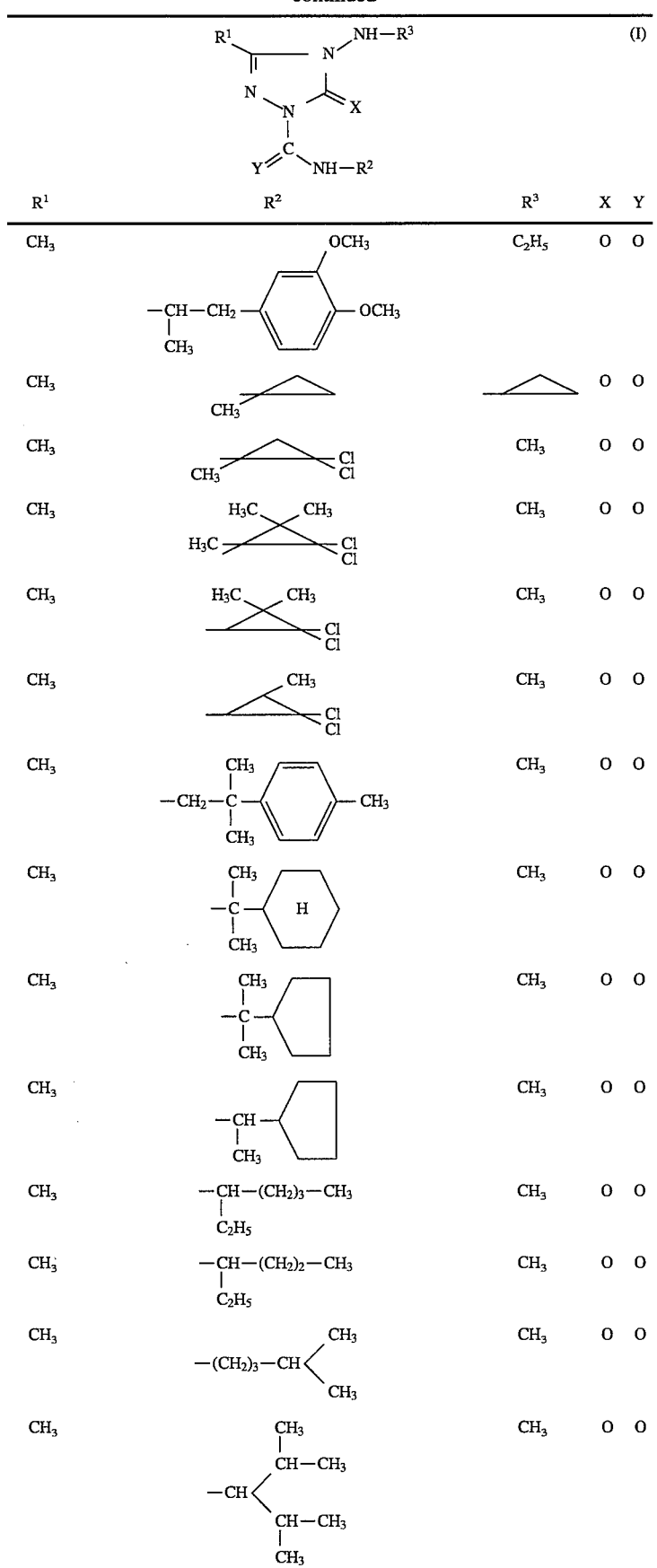

-continued
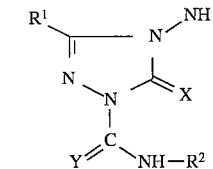 (I)
| R¹ | R² | R³ | X | Y |
|---|---|---|---|---|
| CH₃ | 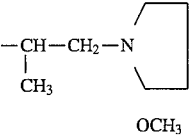 | CH₃ | O | O |
| CH₃ | 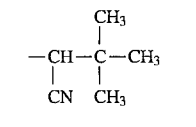 | CH₃ | O | O |
| CH₃ | 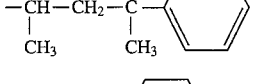 | CH₃ | O | O |
| CH₃ | 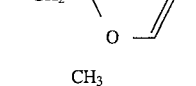 | CH₃ | O | O |
| CH₃ |  | CH₃ | O | O |
| CH₃ | 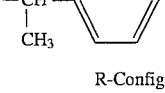 | CH₃ | O | S |
| CH₃ | 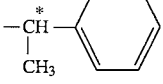<br>R-Configuration | CH₃ | O | S |
| CH₃ | 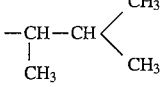<br>S-Configuration | CH₃ | O | S |
| CH₃ | 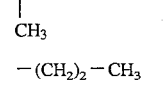 | CH₃ | O | S |
| CH₃ | —CH—CH₂—OCH₃<br>   \|<br>   CH₃ | CH₃ | O | S |
| CH₃ | —(CH₂)₂—CH₃ | CH₃ | O | S |
| CH₃ | 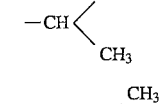 | CH₃ | O | S |
| CH₃ |  | CH₃ | O | S |

-continued

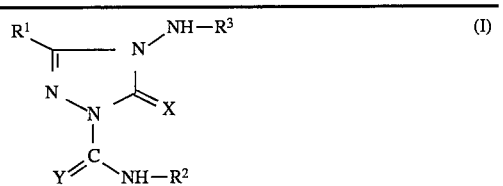

| R¹ | R² | R³ | X | Y |
|---|---|---|---|---|
| CH₃ | —CH(CH₃)—C₂H₅ | CH₃ | O | S |
| CH₃ | cyclopropyl | CH₃ | O | S |
| CH₃ | cyclopentyl | CH₃ | O | S |
| CH₃ | —(CH₂)₂—CH₃ | CH₃ | S | O |
| CH₃ | —(CH₂)₃—CH₃ | CH₃ | S | O |
| CH₃ | —CH₂—CH(CH₃)₂ | CH₃ | S | O |
| CH₃ | —CH(CH₃)—C₂H₅ | CH₃ | S | O |
| CH₃ | C₆H₅—CH₂—CH(CH₃)— | CH₃ | O | O |
| CH₃ | C₆H₅—CH₂—CH₂—CH(CH₃)— | CH₃ | O | O |
| CH₃ | C₆H₅—C≡C—CH(CH₃)— | CH₃ | O | O |
| CH₃ | C₆H₅—CH₂—CH(CH₃)— | CH₃ | O | S |
| CH₃ | C₆H₅—CH₂—C(CH₃)₂— | CH₃ | O | O |
| CH₃ | C₆H₅—CH₂—CH(CH₃)— | C₂H₅ | O | O |
| C₂H₅ | C₆H₅—CH₂—CH(CH₃)— | CH₃ | O | O |
| C₂H₅ | C₆H₅—CH₂—CH₂—CH(CH₃)— | CH₃ | O | O |
| cyclopropyl | C₆H₅—CH₂—CH₂—CH(CH₃)— | CH₃ | O | O |
| cyclopropyl | C₆H₅—CH₂—CH₂—C(CH₃)₂— | CH₃ | O | O |
| cyclopropyl | C₆H₅—CH₂—C(CH₃)₂— | CH₃ | O | O |

-continued $$\text{(I)}$$

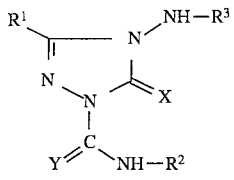

| R¹ | R² | R³ | X | Y |
|---|---|---|---|---|
| $C_2H_5$ | $C_6H_5-CH_2-CH_2-CH(CH_3)-$ | $C_2H_5$ | O | O |
| $C_2H_5$ | $C_6H_5-CH_2-CH_2-C(CH_3)_2-$ | $C_2H_5$ | O | O |
| $CH_3$ | $C_6H_5-CH_2-CH_2-C(C_2H_5)_2-$ | $CH_3$ | O | O |
| $CH_3$ | 4-F-$C_6H_4$-$CH_2-CH(CH_3)-$ | $CH_3$ | O | O |
| $CH_3$ | 4-Cl-$C_6H_4$-$CH_2-CH_2-CH(CH_3)-$ | $CH_3$ | O | O |
| $CH_3$ | 4-$CH_3$-$C_6H_4$-$CH_2-CH_2-CH(CH_3)-$ | $CH_3$ | O | O |
| $C_2H_5$ | 4-$CH_3O$-$C_6H_4$-$C\equiv C-C(CH_3)_2-$ | $CH_3$ | O | O |
| cyclopropyl | 4-$F_3C$-$C_6H_4$-$CH_2-CH(CH_3)-$ | $CH_3$ | O | O |
| $CH_3$ | 4-$F_2CHO$-$C_6H_4$-$CH_2-CH_2-C(CH_3)_2-$ | $CH_3$ | O | O |
| $CH_3$ | 4-$F_3CO$-$C_6H_4$-$CH_2-CH_2-C(CH_3)_2-$ | $CH_3$ | O | O |
| $C_2H_5$ | 4-$H_3CS$-$C_6H_4$-$CH_2-CH_2-CH(C_2H_5)-$ | $CH_3$ | O | O |
| $CH_3$ | 4-$H_3CO_2S$-$C_6H_4$-$CH_2-C(CH_3)_2-$ | $CH_3$ | O | O |
| $CH_3$ | 4-$H_3CO_2S$-$C_6H_4$-$CH_2-CH_2-C(CH_3)_2$ | $CH_3$ | O | O |

-continued $$R^1 \underset{N}{\overset{\underset{\|}{}}{\underset{N}{\|}}} \underset{N}{\overset{NH-R^3}{\underset{X}{}}} \quad (I)$$
$$\underset{Y}{\overset{\|}{C}} \underset{NH-R^2}{}$$

| $R^1$ | $R^2$ | $R^3$ | X | Y |
|---|---|---|---|---|
| $C_2H_5$ | $F_3CS\text{-}\langle\text{phenyl}\rangle\text{-}CH_2\text{-}CH(CH_3)\text{-}$ | $C_2H_5$ | O | O |
| $CH_3$ | $F_3CSO_2\text{-}\langle\text{phenyl}\rangle\text{-}CH_2\text{-}CH_2\text{-}CH(CH_3)\text{-}$ | $CH_3$ | O | O |

If, for example, n-butyl isocyanate and 3-methyl-4-methylamino-(1H)-1,2,4-triazolin-5-one are used as the starting compounds, the course of the reaction of process (a) according to the invention may be represented by the following equations:

If, for example, α,α-dimethylbenzyl isocyanate and 3-isopropyl-4-ethoxymethyleneimino-1H-1,2,4-triazolin-5-one are used as the starting compounds, the course of the reaction of process (b) according to the invention may be represented by the following equation:

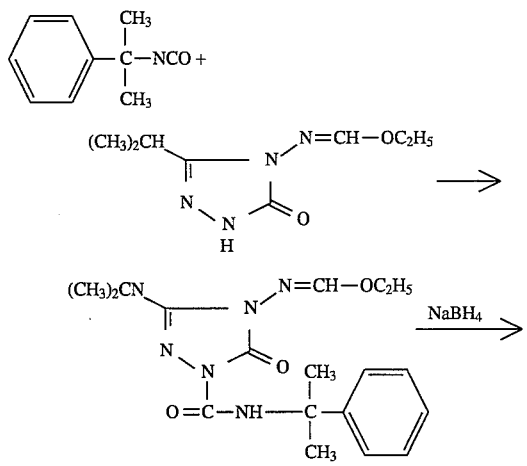

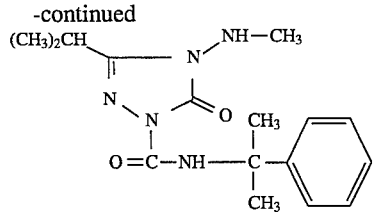

If, for example, 1-(N-phenylcarbamoyl)-3-trifluoromethyl-4-amino-1,2,4-triazolin-5-one and triethyl orthoacetate are used as the starting substances, the course of the reaction of process (c) according to the invention may be represented by the following equation:

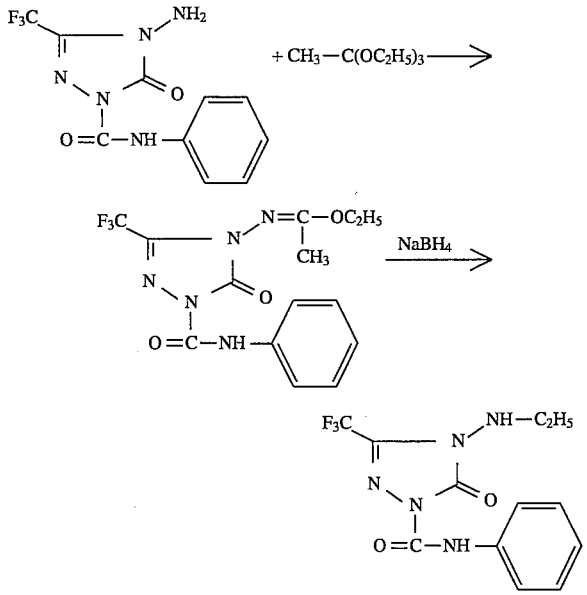

If, for example, 3-methyl-4-phenylamino-1H-1,2,4-triazolin-5-one, O-phenyl chlorothioformate and cyclopentylamine are used as the starting substances, the course of the reaction of process (d) according to the invention may be represented by the following equation:

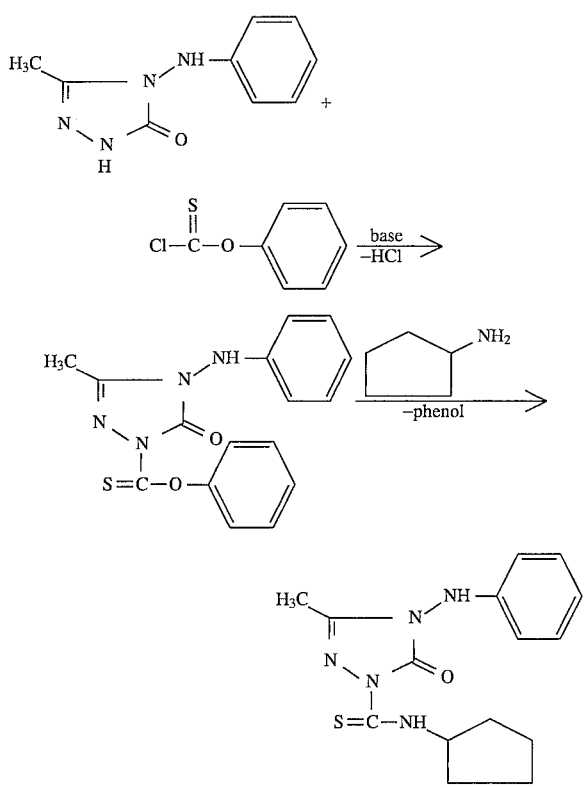

If, for example, N-benzyl-O-phenyl-urethane and 3-cyclobutyl-4-isopropylamino-1H-1,2,4-triazolin-5-one are used as the starting substances, the course of the reaction of process (e) according to the invention may be represented by the following equation:

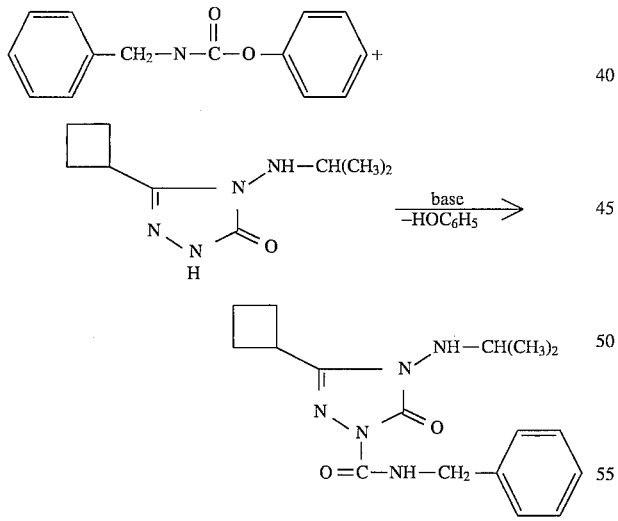

If, for example, 1-cyclopropylaminocarbonyl-3-(1,1-dimethyl-ethyl)-4-benzylideneimino-1,2,4-triazolin-5-one and sodium cyanoborohydride are used as the starting substances, the course of the reaction of process (f) according to the invention may be represented by the following equation:

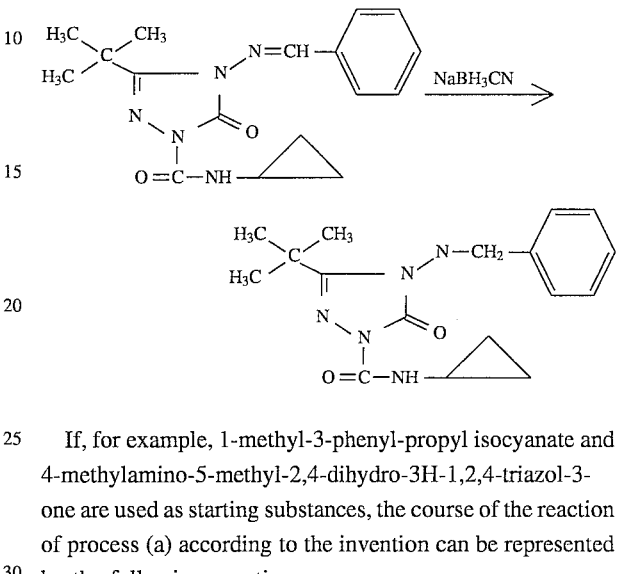

If, for example, 1-methyl-3-phenyl-propyl isocyanate and 4-methylamino-5-methyl-2,4-dihydro-3H-1,2,4-triazol-3-one are used as starting substances, the course of the reaction of process (a) according to the invention can be represented by the following equation:

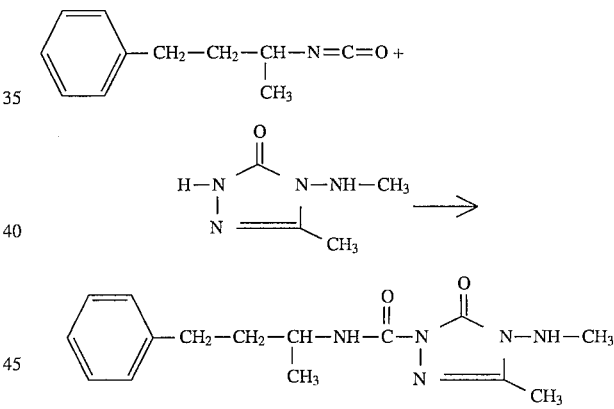

If, for example, 1,1-dimethyl-3-phenyl-propyl isocyanate and 4-ethoxymethyleneimino-5-isopropyl-2,4-dihydro-3H-1,2,4-triazol-3-one are used as starting substances, the course of the reaction of process (b) according to the invention can be represented by the following equation:

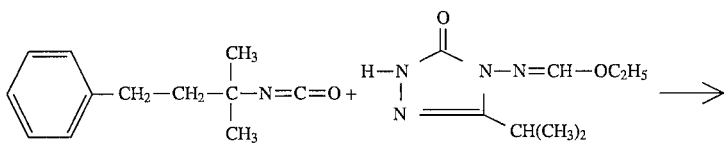

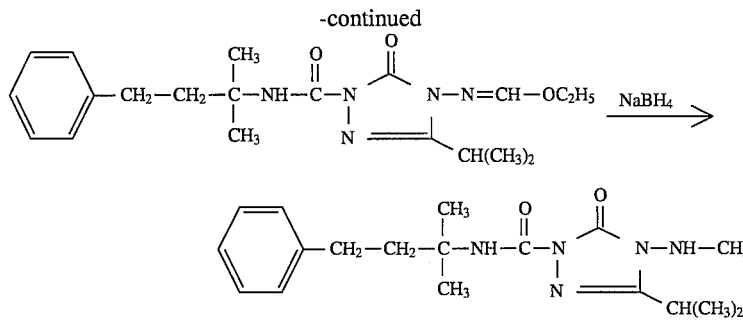

If, for example, 2-(1-methyl-2-phenyl-ethyl-aminocarbonyl)-4-amino-5-ethyl-2,4-dihydro-3H-1,2,4-triazol-3-one and triethyl orthoacetate are used as starting substances, the course of the reaction of process (c) according to the invention can be represented by the following equation:

If, for example, 4-ethylamino-5-methyl-2,4-dihydro-3H-1,2,4-triazol-3-one and N-(1,1-dimethyl-2-phenylethyl)-O-phenyl-urethane are used as starting substances, the course of the reaction of process (e) according to the invention can be represented by the following equation:

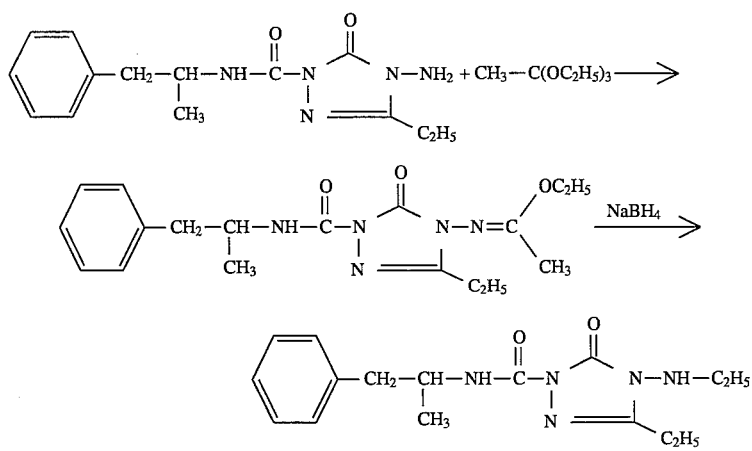

If, for example, 4-methylamino-5-propyl-2,4-dihydro-3H-1,2,4-triazol-3-one, O-phenyl chlorothioformate and 1,1-dimethyl-3-cyclohexyl-propylamine are used as starting substances, the course of the reaction of process (d) according to the invention can be represented by the following equation:

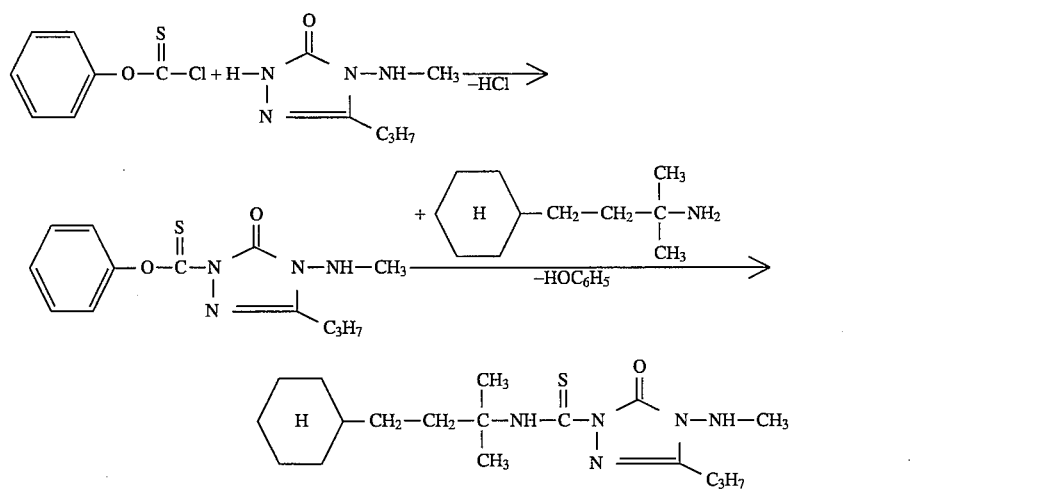

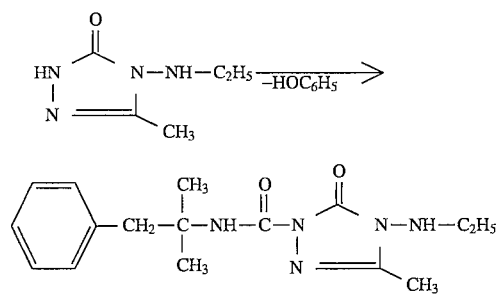

If, for example, 2-(1-ethyl-3-phenyl-propyl-aminocarbonyl)-4-isopropylideneimino-5-methyl-2,4-dihydro-3H-1,2,4-triazol-3-one and sodium cyanoborohydride are used as starting substances, the course of the reaction of process (f) according to the invention can be represented by the following equation:

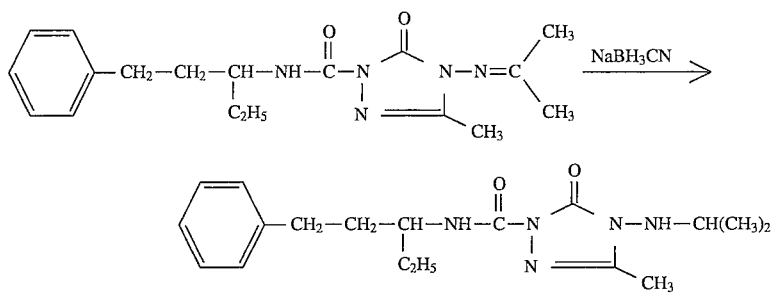

Formula (II) provides a general definition of the 1H-triazolinones to be used as starting substances in process (a) according to the invention for the preparation of compounds of the formula (I).

$R^1$, $R^3$ and X in formula (II) preferably, or in particular, have those meanings which have already been mentioned above in connection with the description of the compounds of the formula (I) according to the invention as being preferred, or particularly preferred, for $R^1$, $R^3$ and X.

With the exception of 4-methylamino-3-methyltriazolin-5-one, 4-methylamino-3-methyl-triazoline-5-thione and 4-ethylamino-3-ethyltriazoline-5-thione, the 1H-triazolinones of the formula (II) were hitherto unknown from the literature.

The new compounds of the formula (II) are obtained when hydrazides of the general formula (XVI)

in which $R^1$ and X have the abovementioned meaning and $R^9$ and $R^{10}$ independently of one another represent alkyl, aryl or aralkyl, are reacted with hydrazine derivatives of the general formula (XVII)

$$H_2N-NH-R^3 \qquad (XVII)$$

in which $R^3$ has the abovementioned meaning, if appropriate in the presence of a diluent, such as, for example, dichloromethane, chloroform, toluene, chlorobenzene, mesitylene or ethylene glycol diethyl ether, and if appropriate in the presence of a catalyst, such as, for example, 1,8-diazabicyclo[5,4,0]-undec-7-ene (DBU), triethylamine or potassium carbonate, at temperatures between 50° C. and 200° C.

The starting substances of the formulae (XVI) and (XVII) are known (cf. Bull. Soc. Chim. France 1962, 1364; Chim. Acta Turcica 3 (1975), 113).

Formula (III) provides a general definition of the iso(thio)cyanates to be used as starting substances in processes (a) and (b) according to the invention.

$R^2$ and Y in formula (III) preferably, or in particular, have those meanings which have already been indicated above in connection with the description of the compounds of the formula (I) according to the invention as being preferred, or particularly preferred, for $R^2$ and Y.

The iso(thio)cyanates of the formula (III) are known chemicals for organic synthesis.

The compounds of the formula (IIIa) are obtained when amino compounds of the formula (IIIa)

$$R^3-NH_2 \qquad (IIIα)$$

in which $R^3$ has the abovementioned meaning, are reacted with phosgene, if appropriate in the presence of a diluent such as, for example, toluene or chlorobenzene, at temperatures between 0° C. and 150° C., or when the amino compounds of the formula (XIII) which have been mentioned as starting substances are reacted with thiophosgene, if appropriate in the presence of diluents such as, for example, toluene or chloroform and water, at temperatures between −10° C. and +50° C.

Formula (IV) provides a general definition of the 1H-triazolinones to be used as starting substances in process (b) according to the invention.

$R^1$ and X in formula (IV) preferably, or in particular, have those meanings which have already been mentioned above in connection with the description of the compounds of the formula (I) according to the invention as being preferred, or particularly preferred, for $R^1$ and X;

$R^4$ preferably represents hydrogen, $C_1$–$C_4$-alkyl, $C_2$–$C_4$-alkenyl, $C_2$–$C_4$-alkinyl, $C_3$–$C_6$-cycloalkyl, phenyl or benzyl, and $R^5$ preferably represents $C_1$–$C_4$-alkyl, $C_2$–$C_4$-alkenyl, $C_2$–$C_4$-alkinyl, $C_3$–$C_6$-cycloalkyl, phenyl or benzyl.

The 1H-triazolinones of the formula (IV) are known and/or can be prepared by processes known per se (cf. J. Heterocycl. Chem. 17 (1980), 1691–1696).

The compounds of the formula (IV) are obtained when aminotriazolinones of the general formula (XVIII)

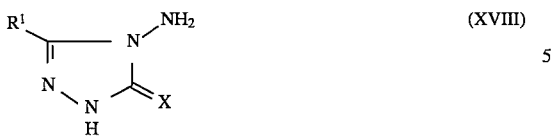

in which

R⁴ and X have the abovementioned meaning, are reacted with orthocarboxylic acid esters of the general formula (X)

in which

R⁴ and R⁵ have the abovementioned meaning, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C.

The starting substances of the formulae (X) and (XVIII) are known (cf. Chem. Ber. 98 (1965), 3025–3033; Chimica Acta Turcica 7 (1979), 269; J. Heterocycl. Chem. 16 (1979), 403–407).

The compounds of the formula (V), which can be alkenyl, $C_2-C_4$-alkinyl, $C_3-C_6$-cycloalkyl, phenyl or benzyl, and R⁵ preferably represents $C_1-C_4$-alkyl, $C_2-C_4$-alkenyl, $C_2-C_4$-alkinyl, $C_3-C_6$-cycloalkyl, phenyl or benzyl.

The 1H-triazolinones of the formula (IV) are known and/or can be prepared by processes known per se (cf. J. Heterocycl. Chem. 17 (1980), 1691–1696).

The compounds of the formula (IV) are obtained when aminotriazolinones of the general formula (XVIII)

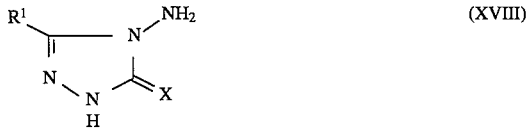

in which

R¹ and X have the abovementioned meaning, are reacted with orthocarboxylic acid esters of the general formula (X)

in which

R⁴ and R⁵ have the abovementioned meaning, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C.

The starting substances of the formulae (X) and (XVIII) are known (cf. Chem. Ber. 98 (1965), 3025–3033; Chimica Acta Turcica 7 (1979), 269; J. Heterocycl. Chem. 16 (1979), 403–407).

The compounds of the formula (V), which can be isolated as intermediates in process (b) according to the invention, were hitherto unknown from the literature. The new compounds of the formula (V) are claimed as new substances according to the invention.

R¹, R², R⁴, R⁵, X and Y in formula (V) preferably, or in particular, have the meaning which has been already indicated above for R¹, R², R⁴, R⁵, X and Y as being preferred, or particularly preferred.

Formulae (VI) and (VII) provide general definitions of the reducing agents to be used in the second step of process (b) according to the invention. M in formulae (VI) and (VII) in each case represents lithium, sodium or potassium, in particular lithium or sodium.

The reducing agents of the formulae (VI) and (VII) are known chemicals for synthesis.

The compounds of the formula (VIII) to be prepared by progress (b) represent a selection from amongst the compounds of the formula (I) according to the invention and are therefore likewise new substances according to the invention.

Formula (IX) provides a general definition of the 1-carbamoyl-triazolinones to be used as starting substances in process (c) according to the invention for the preparation of compounds of the formula (I).

R¹, R², X and Y in formula (IX) preferably, or in particular, have those meanings which have already been mentioned above in connection with the description of the compounds of the formula (I) according to the invention as being preferred, or particularly preferred, for R¹, R², X and Y.

The starting substances of the formula (IX) are known and/or can be prepared by processes known per se (cf. EP-A 294,666).

The information given in the description of process (b) according to the invention is also true in the case of the compounds of the formulae (VI), (VII) and (X) to be used furthermore as starting substances in process (c) and in the case of the compounds obtained as the products.

The information given above in the case of process (a) according to the invention is also true in the case of the 1H-triazolinones of the formula (II) to be used as starting substances in process (d) according to the invention.

Formula (XI) provides a general definition of the (thio-)chloroformic esters furthermore to be used as starting substances in process (d) according to the invention for the preparation of compounds of the formula (I).

Y in formula (XI) preferably, or in particular, has the meaning which has already been mentioned above in connection with the description of the compounds of the formula (I) according to the invention as being preferred, or particularly preferred, for Y, and R⁶ preferably represents $C_1-C_4$-alkyl, phenyl or benzyl.

The starting substances of the formula (XI) are known chemicals for organic synthesis.

Formula (XIII) provides a general definition of the amines to be used as starting substances in the second step of process (d) according to the invention.

R² in formula (XIII) preferably, or in particular, has the meaning which has already been mentioned above in connection with the description of the compounds of the formula (I) according to the invention as being preferred, or particularly preferred, for R².

The starting substances of the formula (XIII) are known chemicals for synthesis.

The compounds of the formula (XII), which can be isolated as intermediates in process (d) according to the invention, were hitherto unknown from the literature. The new compounds of the formula (XII) are claimed as new substances according to the invention.

R¹, R³, R⁶, X and Y in formula (XII) preferably, or in particular, have the meaning already mentioned above in the case of R¹, R³, R⁶, X and Y as being preferred, or particularly preferred.

The intermediates of the formula (V) obtained in processes (b) and (c) according to the invention and the intermediates of the formula (XII) obtained in process (d) can be isolated in each case, but they can also be reacted further without intermediate isolation (in the so-called "one-pot process").

The information given above in the description of the starting substances for process (a) according to the invention is also true in the case of the 1H-triazolinones of the formula (II) to be used as the starting substances in process (e) according to the invention.

Formula (XIV) provides a general definition of the (thio-)urethanes furthermore to be used as starting substances in process (e) according to the invention for the preparation of compounds of the formula (I).

$R^2$ and Y in the formula (XIV) preferably, or in particular, have those meanings which have already been mentioned above in connection with the description of the compounds of the formula (I) according to the invention as being preferred, or particularly preferred, for $R^2$ and Y, and $R^6$ preferably represents $C_1$–$C_4$-alkyl, phenyl or benzyl.

The starting substances of the formula (XIV) are known chemicals for organic synthesis.

Formula (XV) provides a general definition of the triazolinone-hydrazones to be used as starting substances in process (f) according to the invention for the preparation of compounds of the formula (I).

$R^1$, $R^2$, X and Y in formula (XV) preferably, or in particular, have those meanings which have already been mentioned above in connection with the description of the compounds of the formula (I) according to the invention as being preferred, or particularly preferred, for $R^1$, $R^2$, X and Y, and $R^7$ and $R^8$, in each case independently of one another preferably represent hydrogen, $C_1$–$C_4$-alkyl, phenyl or benzyl.

The starting substances of the formula (XV) are known and/or can be prepared by processes known per se (cf. EP-A 294,666).

Process (a) according to the invention is preferably carried out in the presence of a diluent.

Suitable diluents for carrying out process (a) according to the invention are, in particular, inert organic solvents. These include, for example, aliphatic, alicyclic or aromatic, optionally halogenated hydrocarbons, such as benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethyl acetamide, N-methylformanilide, N-methylpyrrolidone or hexamethylphosphoric triamide, or esters, such as ethyl acetate.

If appropriate, process (a) according to the invention is carried out in the presence of a suitable reaction auxiliary. Suitable reaction auxiliaries are all customary inorganic or organic bases. These include, for example, tertiary amines, such as triethylamine, N,N-dimethylaniline, N,N-diethylbenzylamine, N,N-dimethylcyclohexylamine or dibutyltindilaureate, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between 0° C. and 150° C., preferably at temperatures between 10° C. and 100° C.

For carrying out process (a) according to the invention, 1.0 to 2.0 moles, preferably 1.0 to 1.5 moles, of iso(thio-)cyanate of the formula (III) and if appropriate 0.001 to 2.0 moles, preferably 0.001 to 1.0 mole, of reaction auxiliary are generally employed per mole of 1H-triazolinone of the formula (II).

The reaction is carried out and the reaction products are worked up and isolated by generally customary methods.

The first step of process (b) according to the invention is preferably carried out in the presence of a diluent. The solvents which have been indicated above in the case of process (e) according to the invention can also be used for this purpose.

As regards the use of a reaction auxiliary and the reaction temperatures, the information given above in process (a) is also true for the first step of process (b).

For carrying out process (b) according to the invention, 1.0 to 2.0 moles, preferably 1.0 to 1.5 moles, of iso(thio-)cyanate of the formula (III) and if appropriate 0.001 to 2.0 moles, preferably 0.01 to 1.0 mole, of reaction auxiliary are generally employed per mole of 1H-triazolinone of the formula (IV).

It is possible to carry out the reaction and, if appropriate, working up and isolating the intermediates of the formula (V) by generally customary methods.

The second step of process (b) according to the invention is preferably carried out in the presence of a polar solvent. Possible polar solvents are preferably water, alcohols, such as methanol, ethanol, propanol, isopropanol, butanol, isobutanol, sec-butanol and tert-butanol, ether alcohols, such as methoxyethanol and ethoxyethanol, or ethers, such as diethyl ether, dipropyl ether, diisopropyl ether, tetrahydrofuran and dioxane.

In the second step of process (b), the reaction temperatures can be varied within a substantial range. In general, the process is carried out at temperatures between –20° C. and +100° C., preferably between 0° C. and +30° C.

For carrying out the second step of process (b), 0.5 to 5 moles, preferably 1 to 3 moles, of reducing agent of the formula (VI) or (VII) are employed per mole of intermediate of the formula (V).

The reaction is carried out and the reaction products are worked up and isolated by generally customary methods.

If appropriate, the first step of process (c) according to the invention is carried out in the presence of a diluent. The solvents which have been mentioned above in process (a) can be used.

The first step of process (c) is preferably carried out in the presence of a reaction auxiliary. Reaction auxiliaries which are suitable for this purpose are, in particular, strong acids, such as, for example, hydrogen chloride, sulphuric acid, methanesulphonic acid, benzenesulphonic acid and p-toluenesulphonic acid.

In the first step of process (c) according to the invention, the reaction temperatures can be varied within a substantial range. In general, the process is carried out at temperatures between 0° C. and 200° C., preferably at temperatures between 50° C. and 150° C.

For carrying out process (c) according to the invention, 1 to 100 moles, preferably 1 to 20 moles, of orthocarboxylic acid ester of the formula (X) and if appropriate 0.001 to 2.0 moles, preferably 0.01 to 1.0 mole, of reaction auxiliary are generally employed per mole of 1-carbamoyl-triazolinone of the formula (IX).

It is possible to carry out the reaction and, if appropriate, to work up and isolate the intermediates of the formula (V) by generally customary methods.

The second step of process (c) according to the invention is preferably carried out in the presence of a diluent. The solvents which have been mentioned above in the case of the second step of process (b) can also be used for this purpose.

In the second step of process (c), the reaction temperatures can be varied within a substantial range. In general, the process is carried out at temperatures between −20° C. and +100° C., preferably between 0° C. and +30° C.

For carrying out the second step of process (c), 0.5 to 5 moles, preferably 1 to 3 moles, of reducing agent of the formula (VI) or (VII) are generally employed per mole of intermediate of the formula (V).

The reaction is carried out and the reaction products are worked up and isolated by customary methods.

Both steps of process (d) according to the invention are preferably carried out in the presence of a diluent. The solvents which have been mentioned above in the case of process (a) according to the invention can also be used for this purpose.

If appropriate, both steps of process (d) according to the invention can be carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the two steps of process (d) according to the invention, the reaction temperatures can be varied within a substantial range. In general, the process is carried out at temperatures between 0° C. and 150° C., preferably between 10° C. and 100° C.

For carrying out process (d) according to the invention, 1 to 2 moles, preferably 1.0 to 1.5 moles, of (thio)chloroformic acid ester of the formula (XI) and 1 to 2 moles, preferably 1.0 to 1.5 moles, of reaction auxiliary are generally employed per mole of 1H-triazolinone of the formula (II).

It is possible to carry out the reaction and, if appropriate, to work up and isolate the intermediates of the formula (XII) by generally customary methods.

For carrying out the second step of process (d), 1 to 2 moles, preferably 1.0 to 1.5 moles, of amine of the formula (XIII) are generally employed per mole of intermediate of the formula (XII).

The reaction is carried out and the products of the formula (I) are worked up and isolated by generally customary methods.

Process (e) according to the invention is preferably carried out in the presence of a diluent. The solvents which have been mentioned above in the case of process (a) according to the invention can also be used for this purpose.

Process (e) is preferably carried out in the presence of a reaction auxiliary. The reaction auxiliaries which have been mentioned above in the case of process (d) according to the invention can be used for this purpose.

In process (e) according to the invention, the reaction temperatures can be varied within a substantial range. In general, the process is carried out at temperatures between 0° C. and 150° C., preferably at temperatures between 10° C. and 120° C.

For carrying out process (e) according to the invention, 1 to 2 moles, preferably 1.0 to 1.5 moles, of (thio)urethane of the formula (XIV) are generally employed per 1 mole of 1H-triazolinone of the formula (II).

The reaction is carried out and the products of the formula (I) are worked up and isolated by generally customary methods.

Process (f) according to the invention is carried out using a reducing agent and, if appropriate, a catalyst. Examples of suitable systems of reducing agents and catalysts are hydrogen in combination with customary hydrogenation catalysts, such as, for example, Raney nickel, palladium or platinum, and furthermore also metal hydrides which may be complex, such as, for example, lithium alanate, sodium boronate and sodium cyanoborohydride, if appropriate in combination with acid catalysts, such as, for example, hydrochloric acid or acetic acid.

Process (f) is preferably carried out in the presence of a diluent. The solvents which have been mentioned above in the case of the second step of process (b) according to the invention can be used for this purpose.

In process (f) according to the invention, the reaction temperatures can be varied within a substantial range. In general, the reaction is carried out at temperatures between −20° C. and +100° C., preferably at temperatures between 0° C. and +30° C.

The reaction is carried out and the reaction products are worked up and isolated by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panictun, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Sacale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively controlling dicotyledon weeds in monocotyledon cultures, using the pre-emergence method as well as the post-emergence method.

The active compounds according to the invention also exhibit a powerful activity against pests and can be employed in practice for combating undesired pests. The active compounds are suitable for use as plant protection agents especially as fungicides.

Fungicidal agents in plant protection are employed for combating Plasmodiophoromycetes, Oomycetes, Chytridiomycetes, Zygomycetes, Ascomycetes, Basidlomycetes and Deuteromycetes.

Some causative organisms of fungal diseases included under the abovementioned main headings, are mentioned below as non-limiting examples:

Pythium species, such as, for example, *Pythium ultimum;*
Phytophthora species, such as, for example, *Phytophthora infestans;*
Pseudoperonospora species, such as, for example, *Pseudoperonospora cubense;*
Plasmopara species, such as, for example, *Plasmopara viticola;*
Peronospora species, such as, for example, *Peronospora pisi* or *P. brassicae;*
Erysiphe species, such as, for example, *Erysiphe graninis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea;*
(Conidial form: Drechslera, Synonym: Helminthosporium);
Cochliobolus species, such as, for example, *Cochliobolus sativus;*
(Conidial form; Drechslera, Synonym: Helminthosporium);
Uromyces species, such as, for example, *Uromyces appendiculatus;*
Puccinia species such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such for example, *Cercospora canescans;*
Alternaria species, such as, for example, *Alternaria brassicae;*
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The compounds of the formula (I) are particularly suitable for combating crop diseases, such as, for example, for combating causative organisms of the powdery mildew of crop (*Erysiphe graminis*).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances and when applied as fungicide in coating compositions for seed, as well as ULV formulations.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)- one (META-MITRON) for combating weeds in sugar beet, and 4-amino-6-(1,1-dimethylethyl)-3-methylthio-1,2,4-triazin-5 (4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-4-ethylamino-6-isopropylamino-1,3,5-triazine (ATRAZINE); 3-(isopropyl-2,1,3-benzothiadiazin-4 -one, 2,2-dioxide (BENTAZONE); methyl 5-(2,4-dichlorophenoxy-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino)-1,3,5-triazine (CYANAZIN); 2-[4-(2,4-dichlorophenoxy)-phenoxy]-propionic acid, its methyl ester or its ethyl ester (DICLOFOP); 2-[(2-chlorophenyl)methyl]-4,4-dimethylisoxazolidin-3-one (DIMETHAZONE); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFEN-ACET); 2-{[[((4-methoxy-6-methyl-1,3,5-triazin-2-yl)amino)-carbonyl]-amino]-sulphonyl}-benzoic acid or its methyl ester (METSULFURON); N-(1-ethylpropyl)-3,4-di-methyl-2,6-dinitroaniline (PENDIMETHALIN), 4-ethylamino-2-t-butylamino-6-methylthio-s-triazine (TERBUTRYNE); methyl 3-[[[[(4-methoxy-6-methyl-1,3,5-triazin-2-yl)amino]-carbonyl]-amino]-sulphonyl]-thiophene-2-carboxylate (THIAKETURON) and S-2,3,3-trichloroallyl N,N-diisopropylthiolcarbamate (TRIALLATE). Surprisingly, some mixtures also show synergistic action.

A mixture with other known active compounds, such as fungicides, insecticides, acaricides, nematicides, bird repellents, plant nutrients and agents which improve soil structure, is also possible. When the active compounds are applied as fungicides mixtures with fertilizers and other growth regulators are also possible.

Depending on the application, the active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The active compounds according to the invention can be applied either before or after emergence of the plants when applied as herbicides.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha when the active compound is used as herbicide.

The preparation and use of the active compounds according to the invention can be seen from the following examples.

preparation Examples

EXAMPLE 1

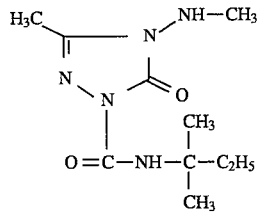

(Process (a))

3.9 g (0.03 mol) of 3-methyl-4-methylamino-1H-1,2,4-triazolin-5-one are suspended in 80 ml of acetonitrile, and the mixture is treated in succession with 0.2 g of diazabicycloundecene (DBU) and 3.7 g (0.033 mol) of tert-amyl isocyanate. The mixture is stirred #or 12 hours at 20° C. and concentrated in vacuo, the concentrate is taken up in methylene chloride, and the mixture is washed with dilute hydrochloric acid and water under neutral. The organic phase is dried and evaporated, and the residue is triturated with ether/petroleum ether.

This gives 5.0 g (0.0207 mol, 69% of theory) of 1-[N-(1,1-dimethyl-propyl)-carbamoyl]-3-methyl-4-methylamino-1,2,4-triazolin-5-one of melting point 98° C.

EXAMPLE 2

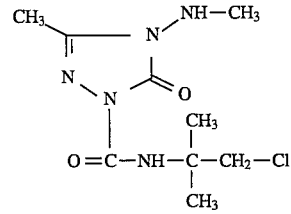

(Process (b))

8.5 g (0.05 mol) of 4-ethoxymethyleneimino-3-methyl-1H-1,2,4-triazolin-5-one are suspended in 100 ml of acetonitrile, and the stirred mixture is treated in succession with about 200 mg of diazabicycloundecene (DBU) and 6.7 g (0.05 mol) of monochloro-tert-butyl isocyanate. After 12 hours at 20° C., the mixture is concentrated in vacuo, the concentrate is taken up in methylene chloride and the mixture is washed with dilute hydrochloric acid and water until neutral. After the mixture has been dried, it is evaporated and the residue is triturated with n-hexane.

This gives 11.0 g (0.0362 mol, 72.5% of theory) of 1-[N-(1-chloromethyl-1-methyl-ethyl)-carbamoyl]-4-ethoxymethyleneimino-3-methyl-1,2,4-triazolin-5-one of melting point 77° C.

6.1 g (0.02 mol) of the above compound are dissolved in 50 ml of absolute ethanol, and the stirred solution is treated at 0° C. with 2.3 g (0.06 mol) of sodium borohydride.

After the reaction mixture has been stirred for 12 hours, it is carefully acidified using hydrochloric acid and then evaporated in vacuo, and the residue is taken up in methylene chloride. The mixture is washed with water, dried and evaporated, and the residue is triturated with ether/petroleum ether.

This gives 1.9 g (0.0073 mol), 36.3% of theory) of 1-[N-(1-chloromethyl-1-methyl-ethyl)-carbamoyl]-3-methyl-4-methylamino-1,2,4-triazolin-5-one of melting point 93° C.

EXAMPLE 3

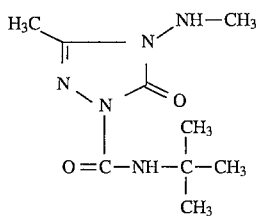

(Process (c))

6.4 g (0.03 mol) of 4-amino-1-[N-(1,1-dimethylethyl)-carbamoyl]-3-methyl-1,2,4-triazolin-5-one are refluxed for 2 hours in about 80 ml of triethyl orthoformate in the presence of 0.1 g of p-toluenesulphonic acid.

When cold, the solution is evaporated in vacuo, and the residue is triturated in n-hexane. This gives 4.9 g (0.0182 mol, 60.7% of theory) of 1-[N-(1,1-dimethyl-ethyl)-carbamoyl]-4-ethoxymethyleneimino-3-methyl-1,2,4-triazolin-5-one of melting point 102° C.

2.7 g (0.01 mol) of the above compound are dissolved in 40 ml of absolute ethanol, and the solution is treated at 0° C. with 0.8 g (0.011 mol) of sodium borohydride. After 1 hour at 0° C., a further 0.8 g of sodium borohydride is added.

The mixture is stirred for 12 more hours and concentrated in vacuo, and the concentrate is taken up in methylene chloride. It is washed with dilute hydrochloric acid and water until neutral, dried and evaporated.

Triturating the residue with n-hexane gives 1.0 g (0.0044 mol, 44% of theory) of 1-[N-(1,1-dimethyl-ethyl)carbamoyl]-3-methyl-4-methylamino-1,2,4-triazolin-5-one of melting point 150° C.

EXAMPLE 4

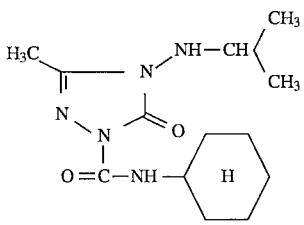

Process (f))

7.0 g (0.025 mol) of 1-(N-cyclohexyl-carbamoyl)-4-isopropylideneimino-3-methyl-1,2,4-triazolin-5-one are dissolved in 20 ml of absolute methanol, and the stirred solution is treated with 2 g (0.03 mol) of sodium cyano borohydride. A spatula tip full of methyl orange is added, and methanolic hydrochloric acid is then added dropwise until the colour changes to red (pH about 3). This pH of the solution is maintained for 12 hours, the solution is then concentrated in vacuo, and the concentrate is taken up in methylene chloride. After the mixture has been washed with water, dried and evaporated, the residue is triturated in ether/petroleum ether.

This gives 3.1 g (0.011 mol, 44% of theory) of 1-(N-cyclohexyl-carbamoyl)-4-isopropylamino-3-methyl-1,2,4-triazolin-5-one of melting point 92° C.

EXAMPLE 102

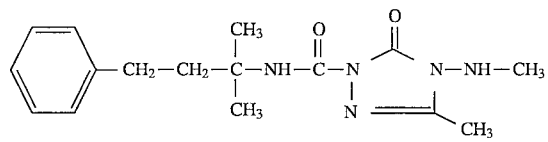

(Process (a))

A mixture of 2.6 g (0.02 mol) of 4-methylamino-5-methyl-2,4-dihydro-3H-1,2,4-triazol-3-one, 3.8 g (0.02 mol) of 1,1-dimethyl-3-phenyl-propyl isocyanate, 0.1 g of diazabicycloundecene (DBU) and 100 ml of acetonitrile is stirred for 12 hours at 20° C. and subsequently concentrated under a water pump vacuum. The residue is taken up in methylene chloride, and the mixture is washed with water, dried with sodium sulphate and filtered. The filtrate is concentrated, the residue is brought to crystallisation by trituration with diethyl ether/petroleum ether, and the crystalline product is isolated by filtration with suction.

5.1 g (80% of theory) of 2-(1,1-dimethyl-3-phenyl-propylaminocarbonyl)-4-methylamino-5-methyl-2,4-dihydro-3H-1,2,4-triazol-3-one of melting point 102° C. are obtained.

The following substituted triazolinones of the general formula (I):

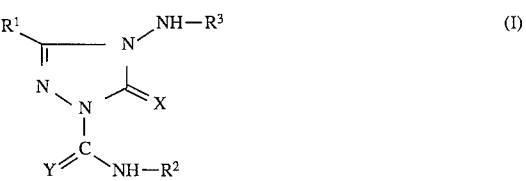

are obtained in a corresponding manner and following the general preparation instructions:

TABLE 1

| Ex. No. | R¹ | R² | R³ | X | Y | Melting point °C. |
|---|---|---|---|---|---|---|
| 5 | (CH₃)₂CH | C(CH₃)₃ | CH₃ | O | O | 121 |
| 6 | (CH₃)₂CH | C(CH₃)₂—CH₂Cl | CH₃ | O | O | 150 |
| 7 | CH₃ | CH(CH₃)—CH₂Cl | CH₃ | O | O | 82 |
| 8 | CH₃ | 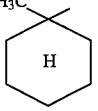 | CH₃ | O | O | 129 |
| 9 | CH₃ | 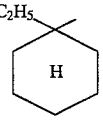 | CH₃ | O | O | 99 |
| 10 | CH₃ | C(CH₃)₂—CH₂F | CH₃ | O | O | 161 |
| 11 | (CH₃)₂CH | C(CH₃)₂—CH₂F | CH₃ | O | O | 124 |
| 12 | CH₃ |  | CH₃ | O | O | 100 |
| 13 | CH₃ | CH(CH₃)—C₃H₇-i | CH₃ | O | O | 132 |
| 14 | CH₃ | C(CH₃)₂—C₄H₉-n | CH₃ | O | O | 89 |
| 15 | CH₃ | 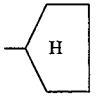 | CH₃ | O | O | 137 |
| 16 | CH₃ | 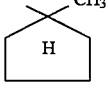 | CH₃ | O | O | 116 |
| 17 | CH₃ | n-C₃H₇ | CH₃ | O | O | 79 |
| 18 | CH₃ | i-C₃H₇ | CH₃ | O | O | 135 |
| 19 | CH₃ | CH(CH₃)—C₂H₅ | CH₃ | O | O | 127 |
| 20 | CH₃ | C(CH₃)₂C≡CH | CH₃ | O | O | 98 |
| 21 | CH₃ | 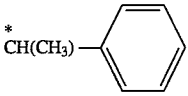<br>S-Configuration | CH₃ | O | O | 103 |
| 22 | C₂H₅ | C(CH₃)₂CH₂Cl | CH₃ | O | O | 141 |
| 23 | C₂H₅ | C(CH₃)₃ | CH₃ | O | O | 105 |
| 24 | C₂H₅ | C(CH₃)₂CH₂F | CH₃ | O | O | 107 |
| 25 |  | C(CH₃)₃ | CH₃ | O | O | 109 |
| 26 | H | C(CH₃)₃ | CH₃ | O | O | 112 |
| 27 | H | C(CH₃)₂CH₂Cl | CH₃ | O | O | 95 |
| 28 | H | C(CH₃)₂CH₂F | CH₃ | O | O | 116 |
| 29 | n-C₃H₇ | C(CH₃)₃ | CH₃ | O | O | 84 |
| 30 | n-C₃H₇ | C(CH₃)₂CH₂Cl | CH₃ | O | O | 90 |
| 31 | n-C₃H₇ | C(CH₃)₂CH₂F | CH₃ | O | O | 77 |
| 32 | CH₃ |  | CH₃ | O | O | 104 |
| 33 | CH₃ | CH(CH₃)—CH₂OC₆H₅ | CH₃ | O | O | 105 |
| 34 | 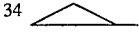 | 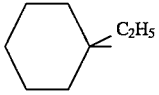 | CH₃ | O | O | 150 |
| 35 |  | C(CH₃)₂—CH₂Cl | CH₃ | O | O | 142 |

TABLE 1-continued

| Ex. No. | R¹ | R² | R³ | X | Y | Melting point °C. |
|---|---|---|---|---|---|---|
| 36 | △ | C(CH₃)₂—CH₂F | CH₃ | O | O | 113 |
| 37 | △ | cyclohexyl-CH(CH₃)— | CH₃ | O | O | 104 |
| 38 | △ | 1-methylcyclohexyl | CH₃ | O | O | 125 |
| 39 | △ | 1-methylcyclopentyl | CH₃ | O | O | 100 |
| 40 | △ | cyclopentyl | CH₃ | O | O | 118 |
| 41 | △ | HC≡C(CH₃)₂— | CH₃ | O | O | 96 |
| 42 | △ | C₂H₅—C(CH₃)₂— | CH₃ | O | O | 88 |
| 43 | △ | C₃H₇—C(CH₃)₂— | CH₃ | O | O | 124 |
| 44 | △ | (CH₃)₂CH— | CH₃ | O | O | 118 |
| 45 | △ | Cl—CH₂—CH(CH₃)— | CH₃ | O | O | 128 |
| 46 | △ | △ | CH₃ | O | O | 98 |
| 47 | △ | (CH₃)₂CH—CH(CH₃)— | CH₃ | O | O | 83 |
| 48 | △ | n-C₃H₇— | CH₃ | O | O | 72 |
| 49 | △ | C₂H₅—CH(CH₃)— | CH₃ | O | O | 94 |
| 50 | △ | (S)-C₆H₅—CH(CH₃)— | CH₃ | O | O | 68 |
| 51 | △ | C₆H₅—O—CH₂—CH(CH₃)— | CH₃ | O | O | 123 |
| 52 | △ | n-C₆H₁₃—CH(CH₃)— | CH₃ | O | O | 75 |
| 53 | △ | (C₂H₅)₂CH—CH₂— | CH₃ | O | O | 72 |
| 54 | △ | (CH₃)₃C—CH₂—CH(CH₃)— | CH₃ | O | O | 123 |
| 55 | △ | (C₂H₅)₃—C— | CH₃ | O | O | 125 |

TABLE 1-continued

| Ex. No. | R¹ | R² | R³ | X | Y | Melting point °C. |
|---|---|---|---|---|---|---|
| 56 | 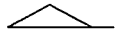 | (CH₃)₂CH—C(CH₃)(CN)— | CH₃ | O | O | ¹H-NMR CDCl₃, δ, ppm: 1,13, 1,18/d 1,74S 2,33m 2,87d, 4,69q, 8,34(NH) |
| 57 |  | (CH₃)₃C—CH₂—C(CH₃)₂— | CH₃ | O | O | 139 |
| 58 |  | nC₅H₁₁—CH(CH₃)— | CH₃ | O | O | 84 |
| 59 | 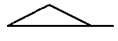 | C₂H₅—CH(CH₂—CN)— | CH₃ | O | O | 113 |
| 60 | 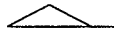 | (C₂H₅)₂CH— | CH₃ | O | O | 96 |
| 61 | 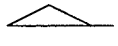 | (C₂H₅)₂C(CH₃)— | CH₃ | O | O | 108 |
| 62 | 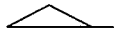 | (CH₃)₃C—CH(CH₃)— | CH₃ | O | O | 144 |
| 63 | 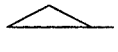 | 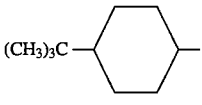 (CH₃)₃C— | CH₃ | O | O | 100 |
| 64 | 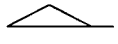 | (CH₃)₂C(CN)— | CH₃ | O | O | 106 |
| 65 | 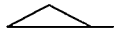 | n-C₃H₇—CH(CH₃)— | CH₃ | O | O | 76 |
| 66 |  | (CH₃)₂CH—CH(CH₃)₂— | CH₃ | O | O | 127 |
| 67 | 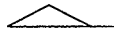 | 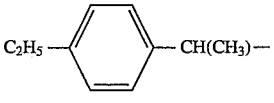 C₂H₅— —CH(CH₃)— | CH₃ | O | O | 97 |
| 68 | 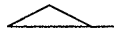 | 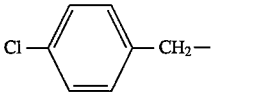 Cl— —CH₂— | CH₃ | O | O | 146 |
| 69 | 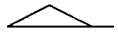 | n-C₄H₉—C(CH₃)₂— | CH₃ | O | O | 161 |
| 70 | 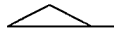 | CH₃—COO—(CH₂)₃— | CH₃ | O | O | 83 |
| 71 | C₂H₅ | 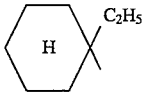 | CH₃ | O | O | 109 |
| 72 | n-C₃H₇ | 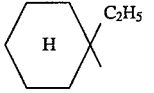 | CH₃ | O | O | 112 |
| 73 | i-C₃H₇ | 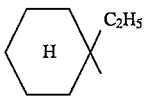 | CH₃ | O | O | 154 |
| 74 | C₂H₅ | i-C₃H₇— | CH₃ | O | O | 75 |
| 75 | C₂H₅ |  | CH₃ | O | O | 117 |

TABLE 1-continued

| Ex. No. | R¹ | R² | R³ | X | Y | Melting point °C. |
|---|---|---|---|---|---|---|
| 76 | $C_2H_5$ | $(CH_3)_2CH-CH(CH_3)-$ | $CH_3$ | O | O | 102 |
| 77 | $C_2H_5$ | $n-C_3H_7$ | $CH_3$ | O | O | 69 |
| 78 | $C_2H_5$ | $s-C_4H_9$ | $CH_3$ | O | O | 78 |
| 79 | $CH_3$ | (S)-cyclohexyl-CH(CH_3)- | $CH_3$ | O | O | 101 |
| 80 | $C_2H_5$ | (S)-cyclohexyl-CH(CH_3)- | $CH_3$ | O | O | 85 |
| 81 | $CH_3$ | $n-C_3H_7-C(CH_3)_2$ | $CH_3$ | O | O | 87 |
| 82 | $CH_3$ | phenyl-$C(CH_3)_2$- | $CH_3$ | O | O | 140 |
| 83 | cyclopropyl | phenyl-$C(CH_3)_2$- | $CH_3$ | O | O | 136 |
| 84 | $CH_3$ | 4-Cl-phenyl-$C(CH_3)_2-CH_2-CH_2-$ | $CH_3$ | O | O | 83 |
| 85 | cyclopropyl | 4-Cl-phenyl-$C(CH_3)_2-CH_2-CH_2-$ | $CH_3$ | O | O | Oil |
| 86 | $CH_3$ | cyclohexyl-$C(CH_3)_2-$ | $CH_3$ | O | O | 134 |
| 87 | $CH_3$ | phenyl-$CH_2-CH_2-CH(CH_3)-$ | $CH_3$ | O | O | 102 |
| 88 | $C_2H_5$ | phenyl-$CH_2-CH_2-CH(CH_3)-$ | $CH_3$ | O | O | 77 |
| 89 | cyclopropyl | phenyl-$CH_2-CH_2-CH(CH_3)-$ | $CH_3$ | O | O | 125 |
| 90 | $CH_3$ | 4-$F_3CO$-phenyl-$CH_2-CH_2-C(CH_3)_2-$ | $CH_3$ | O | O | 73 |
| 91 | cyclopropyl | 4-$F_3CO$-phenyl-$CH_2-CH_2-C(CH_3)_2-$ | $CH_3$ | O | O | 103 |

TABLE 1-continued

| Ex. No. | R¹ | R² | R³ | X | Y | Melting point °C. |
|---|---|---|---|---|---|---|
| 92 |  | 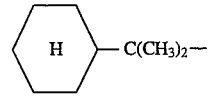 H—⟨cyclohexyl⟩—C(CH₃)₂— | CH₃ | O | O | 144 |
| 93 | CH₃ | H₃CO—⟨phenyl⟩—CH₂—CH₂—C(CH₃)₂— | CH₃ | O | O | Oil |
| 94 | CH₃ | Cl—⟨phenyl⟩—CH₂—CH₂—CH(CH₃)— | CH₃ | O | O | 87 |
| 95 | C₂H₅ | Cl—⟨phenyl⟩—CH₂—CH₂—CH(CH₃)— | CH₃ | O | O | 70 |
| 96 | 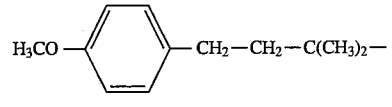 | Cl—⟨phenyl⟩—CH₂—CH₂—CH(CH₃)— | CH₃ | O | O | Oil |
| 97 | CH₃ | F—⟨phenyl⟩—CH₂—CH₂—CH(CH₃)— | CH₃ | O | O | Oil |
| 98 | C₂H₅ | F—⟨phenyl⟩—CH₂—CH₂—CH(CH₃)— | CH₃ | O | O | 74 |
| 99 | 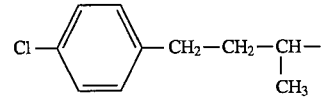 | F—⟨phenyl⟩—CH₂—CH₂—CH(CH₃)— | CH₃ | O | O | Oil |
| 100 | CH₃ | (H₃C)(H₃C)(H₃C)—⟨phenyl⟩—CH₂—CH(CH₃)—CH(CH₃)— | CH₃ | O | O | 113 |
| 101 | C₂H₅ | (H₃C)(H₃C)(H₃C)—⟨phenyl⟩—CH₂—CH(CH₃)—CH(CH₃)— | CH₃ | O | O | 120 |
| 102 | see page 67 | | | | | |
| 103 | CH₃ | ⟨phenyl⟩—CH₂—C(CH₃)₂— | CH₃ | O | O | 98 |
| 104 | 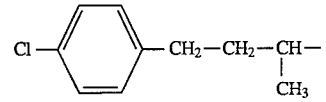 | ⟨phenyl⟩—CH₂—C(CH₃)₂— | CH₃ | O | O | 120 |
| 105 | 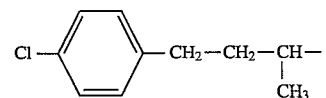 | ⟨phenyl⟩—CH₂—CH₂—C(CH₃)₂— | CH₃ | O | O | 105 |

TABLE 1-continued

| Ex. No. | R¹ | R² | R³ | X | Y | Melting point °C. |
|---|---|---|---|---|---|---|
| 106 | $C_2H_5$ | phenyl-$CH_2-CH_2-C(CH_3)_2-$ | $CH_3$ | O | O | 80 |
| 107 | $C_2H_5$ | phenyl-$CH_2-C(CH_3)_2-$ | $CH_3$ | O | O | 111 |
| 108 | cyclopropyl | phenyl-$CH_2-CH(CH_3)-$ | $CH_3$ | O | O | 90 |
| 109 | $C_2H_5$ | $F_2CHO-$phenyl$-C\equiv C-C(CH_3)_2-$ | $CH_3$ | O | O | amorphous |
| 110 | $C_2H_5$ | cyclohexyl(H)-$CH_2-CH_2-C(CH_3)_2-$ | $CH_3$ | O | O | 97 |
| 111 | $CH_3$ | cyclohexyl(H)-$CH_2-CH_2-C(CH_3)_2-$ | $CH_3$ | O | O | 112 |
| 112 | cyclopropyl | cyclohexyl(H)-$CH_2-CH_2-C(CH_3)_2-$ | $CH_3$ | O | O | 123 |
| 113 | cyclopropyl | phenyl-$CH_2-CH_2-CH_2-C(CH_3)_2-$ | $CH_3$ | O | O | 105 |
| 114 | cyclopropyl | $CH_3O-$phenyl$-CH_2-CH_2-C(CH_3)_2-$ | $CH_3$ | O | O | 102 |
| 115 | $CH_3$ | cyclohexyl(H)-$CH_2-C(CH_3)_2-$ | $CH_3$ | O | O | 94 |
| 116 | $CH_3$ | $F_2CHO-$phenyl$-C\equiv C-C(CH_3)_2-$ | $CH_3$ | O | O | 90 |
| 117 | cyclopropyl | $F_2CHO-$phenyl$-C\equiv C-C(CH_3)_2-$ | $CH_3$ | O | O | 108 |
| 118 | $CH_3$ | phenyl-$CH_2-CH_2-CH_2-C(CH_3)_2-$ | $CH_3$ | O | O | 83 |

TABLE 1-continued

| Ex. No. | R¹ | R² | R³ | X | Y | Melting point °C. |
|---|---|---|---|---|---|---|
| 119 | H | 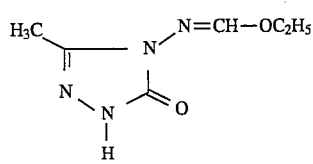 | $CH_3$ | O | O | 106 |
| 120 | $CH_3$ | $NC-C(CH_3)_2-$ | $CH_3$ | O | O | 157 |
| 121 | $C_2H_5$ | $NC-C(CH_3)_2-$ | $CH_3$ | O | O | 102 |

Preparation of the starting compounds

Example IV-1

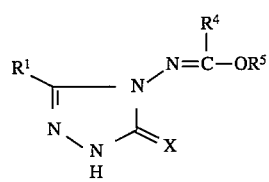

34.2 g (0.3 mol) of 4-amino-3-methyl-1H-1,2,4-triazolin-5-one are refluxed for 2 hours in 300 ml of triethyl orthoformate in the presence of 0.1 g of p-toluenesulphonic acid.

When cold, the solution is evaporated in vacuo, and the residue is triturated with ether. This gives 43.3 g (0.255 mol, 84.9% of theory) of 4-ethoxymethyleneimino-3-methyl-1H-1,2,4-triazolin-5-one of melting point 111° C.

The following precursors of the general formula (IV)

$$\begin{array}{c} R^1 \\ \parallel \\ N \\ \diagdown N \diagup \end{array} \begin{array}{c} R^4 \\ | \\ N=C-OR^5 \\ \diagup \\ X \\ | \\ H \end{array} \quad (IV)$$

are obtained in a corresponding manner and following the general preparation instructions:

TABLE 2

| Ex. No. | R¹ | R⁴ | R⁵ | X | Melting point °C. |
|---|---|---|---|---|---|
| IV-2 | $CH(CH_3)_2$ | H | $C_2H_5$ | O | 75 |
| IV-3 | $C_2H_5$ | H | $C_2H_5$ | O | |
| IV-4 | $CF_3$ | H | $C_2H_5$ | O | 77 |
| IV-5 | △ | H | $C_2H_5$ | O | 79 |
| IV-6 | $CH-C_2H_5$<br>$\|$<br>$CH_3$ | H | $C_2H_5$ | O | |
| IV-7 | $CH_2-O-CH_3$ | H | $C_2H_5$ | O | |
| IV-8 | $C_3H_7$-n | H | $C_2H_5$ | O | |
| IV-9 | $CH_3$ | $CH_3$ | $C_2H_5$ | O | 102 |
| IV-10 | $C_2H_5$ | $CH_3$ | $C_2H_5$ | O | 129 |
| IV-11 | $C_3H_7$-n | $CH_3$ | $C_2H_5$ | O | 75 |
| IV-12 | $CH_2-O-CH_3$ | $CH_3$ | $C_2H_5$ | O | |
| IV-13 | $CH-CH_3$<br>$\|$<br>$CH_3$ | $CH_3$ | $C_2H_5$ | O | 75 |
| IV-14 | △ | $CH_3$ | $C_2H_5$ | O | 131 |
| IV-15 | $CF_3$ | $CH_3$ | $C_2H_5$ | O | 73 |
| IV-16 | $CH(CH_3)_2$ | $CH_3$ | $C_2H_5$ | O | 76 |
| IV-17 | H | H | $C_2H_5$ | O | 124 |
| IV-18 | $CH_2OC_2H_5$ | H | $C_2H_5$ | O | 100 |
| IV-19 | H | $CH_3$ | $C_2H_5$ | O | 103 |
| IV-20 | $CH_2OC_2H_5$ | $CH_3$ | $C_2H_5$ | O | 83 |
| IV-21 | $CH_3$ | $C_2H_5$ | $C_2H_5$ | O | 96 |
| IV-22 | $C_2H_5$ | $C_2H_5$ | $C_2H_5$ | O | 92 |
| IV-23 | $CH(CH_3)_2$ | H | $C_2H_5$ | O | 86 |
| IV-24 | △ | $C_2H_5$ | $C_2H_5$ | O | 75 |
| IV-25 | $CH(CH_3)_2$ | $C_2H_5$ | $C_2H_5$ | O | 110 |
| IV-26 | $CH_3$ | H | $CH_3$ | O | 99 |

Analogously to Example IV-1, it is also possible to prepare the intermediates of the general formula (V):

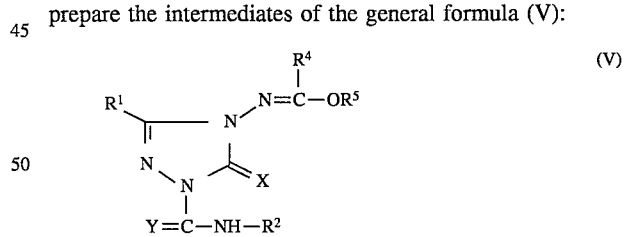

TABLE 3

| Ex. No. | R¹ | R² | R⁴ | R⁵ | X | Y | Melting point °C. |
|---|---|---|---|---|---|---|---|
| V-1 | $CH_3$ | $C(CH_3)_2$—$CH_2Cl$ | H | $C_2H_5$ | O | O | 77 |
| V-2 | $CH_3$ | $C(CH_3)_3$ | H | $C_2H_5$ | O | O | 102 |
| V-3 | $(CH_3)_2CH$ | $C(CH_3)_2$—$CH_2F$ | H | $C_2H_5$ | O | O | 88 |
| V-4 | $CH_3$ | $C(CH_3)_3$ | $CH_3$ | $C_2H_5$ | O | O | 108 |
| V-5 | $CH_3$ | $C(CH_3)_2$—$CH_2Cl$ | $CH_3$ | $C_2H_5$ | O | O | 134 |
| V-6 | $CH_3$ | $C(CH_3)_2$—$CH_2F$ | $CH_3$ | $C_2H_5$ | O | O | 105 |
| V-7 | $CH_3$ | $C_6H_5$ | H | $C_2H_5$ | O | O | 138 |
| V-8 | $CH(CH_3)_2$ | $C(CH_3)_3$ | H | $C_2H_5$ | O | O | 83 |
| V-9 | $CH(CH_3)_2$ | $C(CH_3)_2CH_2Cl$ | H | $C_2H_5$ | O | O | ($^1$H-NMR; $CDCl_3$, δ, ppm; 3.86 for $\underline{CH_2}Cl$) |
| V-10 | $C_2H_5$ | $C(CH_3)_2CH_2Cl$ | H | $C_2H_5$ | O | O | ($^1$H-NMR, $CDl_3$, δ, ppm: 3.86 for $\underline{CH_2}Cl$) |

Example II-1

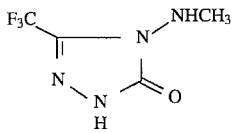

4.5 g (0.02 mol) of 4-ethoxymethyleneimino-3-trifluoromethyl-1H-1,2,4-triazolin-5-one (Example IV-4) are dissolved in 20 ml of tetrahydrofuran, and the solution is added at 20° C. to a stirred suspension of 1.0 g (0.026 mol) of lithium aluminium hydride in 80 ml of tetrahydrofuran. When the evolution of gas has ceased, the mixture is allowed to come to room temperature, and stirring is continued for 12 more hours at this temperature (20° C).

In the next step, a mixture of 25 ml of water and 25 ml of tetrahydrofuran is first added with ice-cooling, and the reaction mixture is finally diluted with 250 ml of water. The mixture is acidified using 2N-hydrochloric acid and then shaken with ethyl acetate, and the organic phase is dried using sodium sulphate and filtered. The solvent is removed from the filtrate by distillation under a water pump vacuum.

This gives 0.2 g (19% of theory) of 4-methylamino-3-trifluoromethyl-1H-1,2,4-triazolin-5-one as a crystalline residue of melting point 90° C.

The following starting materials of the general formula (II)

are obtained in a corresponding manner:

TABLE 4

| Example No. | R¹ | R³ | X | Melting point °C. |
|---|---|---|---|---|
| II-2 | $CH_3$ | $CH_3$ | O | 113 |
| II-3 | $n-C_3H_7$ | $CH_3$ | O | 76 |
| II-4 | $CH(CH_3)_2$ | $CH_3$ | O | 105 |

TABLE 4-continued

| Example No. | R$^1$ | R$^3$ | X | Melting point °C. |
|---|---|---|---|---|
| II-5 | △ | CH$_3$ | O | 95 |
| II-6 | C$_2$H$_5$ | CH$_3$ | O | 101 |
| II-7 | H | CH$_3$ | O | 133 |

Starting substances of the formula (III):

Example (III-1)

TABLE 5

Examples of the compounds of the formula (III)

| Ex. No. | R$^1$ | X | Physical data |
|---|---|---|---|
| III-2 | H$_5$C$_2$OOC—C$_6$H$_4$—CH$_2$—CH$_2$—C(CH$_3$)$_2$— (meta) | O | |
| III-3 | H$_7$C$_3$OOC—C$_6$H$_4$—CH$_2$—CH$_2$—C(CH$_3$)$_2$— (para) | O | b.p.: 110–113° C. at 0.08 mbar |
| III-4 | NC—C$_6$H$_4$—CH$_2$—CH$_2$—C(CH$_3$)$_2$— (para) | O | b.p.: 110° C. at 0.1–0.2 mbar |
| III-5 | C$_6$H$_5$—CH$_2$—CH$_2$—C(CH$_3$)$_2$— | O | |
| III-6 | C$_6$H$_5$—CH$_2$—CH$_2$—CH(CH$_3$)— | O | |
| III-7 | Cl—C$_6$H$_4$—CH$_2$—CH$_2$—C(CH$_3$)$_2$— (para) | O | b.p.: 94° C. at 0.2 mbar |
| III-8 | H$_3$C—C$_6$H$_4$—CH$_2$—CH$_2$—CH(CH$_3$)— (para) | O | |
| III-9 | Cl—C$_6$H$_4$—CH$_2$—CH$_2$—C(CH$_3$)$_2$— (meta) | O | |
| III-10 | Cl—C$_6$H$_4$—CH$_2$—CH$_2$—C(CH$_3$)$_2$— (ortho) | O | |
| III-11 | H$_3$C—C$_6$H$_4$—CH$_2$—CH$_2$—C(CH$_3$)$_2$— (meta) | O | |

TABLE 5-continued

Examples of the compounds of the formula (III)

| Ex. No. | R¹ | X | Physical data |
|---|---|---|---|
| III-12 | 2-methylphenyl-CH₂-CH₂-C(CH₃)₂- | O | |
| III-13 | 3-cyanophenyl-CH₂-CH₂-C(CH₃)₂- | O | |
| III-14 | 4-fluorophenyl-CH₂-CH₂-C(CH₃)₂- | O | |
| III-15 | 4-methoxyphenyl-CH₂-CH₂-C(CH₃)₂- | O | |
| III-16 | 2,4-dichlorophenyl-CH₂-CH₂-C(CH₃)₂- | O | |
| III-17 | 3,4-dichlorophenyl-CH₂-CH₂-C(CH₃)₂- | O | |
| III-18 | 2,6-dichlorophenyl-CH₂-CH₂-C(CH₃)₂- | O | |
| III-19 | 3-(trifluoromethyl)phenyl-CH₂-CH₂-C(CH₃)₂- | O | |
| III-20 | 4-chloro-3-(trifluoromethyl)phenyl-CH₂-CH₃-C(CH₃)₂- | O | |
| III-21 | 4-(trifluoromethoxy)phenyl-CH₂-CH₂-C(CH₃)₂- | O | |
| III-22 | 4-chloro-2-methylphenyl-CH₂-CH₂-C(CH₃)₂- | O | |

TABLE 5-continued

Examples of the compounds of the formula (III)

| Ex. No. | R¹ | X | Physical data |
|---|---|---|---|
| III-23 | (CH₃)₃C—C₆H₄—CH₂—CH₂—C(CH₃)₂— | O | |
| III-24 | 2,5-Cl₂—C₆H₃—CH₂—CH₂—C(CH₃)₂— | O | |
| III-25 | 4-biphenylyl—CH₂—CH₂—C(CH₃)₂— | O | |
| III-26 | 3,4-(OCF₂CHF)—C₆H₃—CH₂—CH₂—C(CH₃)₂— | O | |

At 15° C., 150 g (1.5 mol) of phosgene are introduced into 2.5 l of chlorobenzene, and a solution of 235 g (1.0 mol) of 1,1-dimethyl-3-(4-ethoxycarbonyl-phenyl)-propylamine in 1.0 l of chlorobenzene is metered dropwise into this stirred solution, during which process the internal temperature rises to approx. 25° C. The reaction mixture is then heated, first to approx. 70° C., and, while more phosgene is passed in (approx. 50 g/h), gradually heated to reflux temperature (approx. 127° C.), with stirring, and, after 30 minutes, phosgenated under reflux conditions. Approx. 1 l of chlorobenzene together with excess phosgene is removed from the clear solution by distillation. Finally, the mixture is concentrated under a water pump vacuum, and the residue is distilled under an oil-pump vacuum.

253 g (97% of theory) of 1,1-dimethyl-3-(4-ethoxycarbonyl-phenyl)-propyl isocyanate of boiling range 125° C.–130° C./0.1 mbar are obtained.

Other examples of compounds of the formula (III) which can be prepared analogously to Example (III-1) are those mentioned in Table 4 below:

$$R^1\text{—}N\text{=}C\text{=}X \qquad (III)$$

TABLE 5

Examples of the compounds of the formula (III)

| Ex. No. | R¹ | X | Physical data |
|---|---|---|---|
| III-2 | 3-(H₅C₂OOC)—C₆H₄—CH₂—CH₂—C(CH₃)₂— | O | |
| III-3 | 4-(H₇C₃OOC)—C₆H₄—CH₂—CH₂—C(CH₃)₂— | O | b.p.: 110–113° C. at 0.08 mbar |
| III-4 | 4-NC—C₆H₄—CH₂—CH₂—C(CH₃)₂— | O | b.p.: 110° C. at 0.1–0.2 mbar |

TABLE 5-continued

Examples of the compounds of the formula (III)

| Ex. No. | R¹ | X | Physical data |
|---|---|---|---|
| III-5 | C₆H₅–CH₂–CH₂–C(CH₃)₂– | O | |
| III-6 | C₆H₅–CH₂–CH₂–CH(CH₃)– | O | |
| III-7 | 4-Cl-C₆H₄–CH₂–CH₂–C(CH₃)₂– | O | b.p.: 94° C. at 0.2 mbar |
| III-8 | 4-CH₃-C₆H₄–CH₂–CH₂–CH(CH₃)– | O | |
| III-9 | 3-Cl-C₆H₄–CH₂–CH₂–C(CH₃)₂– | O | |
| III-10 | 2-Cl-C₆H₄–CH₂–CH₂–C(CH₃)₂– | O | |
| III-11 | 3-CH₃-C₆H₄–CH₂–CH₂–C(CH₃)₂– | O | |
| III-12 | 2-CH₃-C₆H₄–CH₂–CH₂–C(CH₃)₂– | O | |
| III-13 | 3-CN-C₆H₄–CH₂–CH₂–C(CH₃)₂– | O | |
| III-14 | 4-F-C₆H₄–CH₂–CH₂–C(CH₃)₂– | O | |
| III-15 | 4-CH₃O-C₆H₄–CH₂–CH₂–C(CH₃)₂– | O | |

TABLE 5-continued

Examples of the compounds of the formula (III)

| Ex. No. | R¹ | X | Physical data |
|---|---|---|---|
| III-16 | 2,4-dichlorophenyl-CH₂-CH₂-C(CH₃)₂- | O | |
| III-17 | 3,4-dichlorophenyl-CH₂-CH₂-C(CH₃)₂- | O | |
| III-18 | 2,6-dichlorophenyl-CH₂-CH₂-C(CH₃)₂- | O | |
| III-19 | 3-(trifluoromethyl)phenyl-CH₂-CH₂-C(CH₃)₂- | O | |
| III-20 | 4-chloro-3-(trifluoromethyl)phenyl-CH₂-CH₂-C(CH₃)₂- | O | |
| III-21 | 4-(trifluoromethoxy)phenyl-CH₂-CH₂-C(CH₃)₂- | O | |
| III-22 | 4-chloro-2-methylphenyl-CH₂-CH₂-C(CH₃)₂- | O | |
| III-23 | 4-tert-butylphenyl-CH₂-CH₂-C(CH₃)₂- | O | |
| III-24 | 2,5-dichlorophenyl-CH₂-CH₂-C(CH₃)₂- | O | |
| III-25 | 4-biphenyl-CH₂-CH₂-C(CH₃)₂- | O | |

TABLE 5-continued

Examples of the compounds of the formula (III)

| Ex. No. | R¹ | X | Physical data |
|---|---|---|---|
| III-26 | 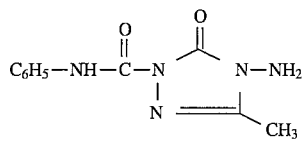 | O | |

Use Examples

In the use examples which follow, the compound listed below was employed as comparison substance:

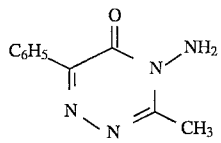 (A)

2-(Phenylaminocarbonyl)-4-amino-5-methyl-2,4-dihydro-3H-1,2,4-triazol-3-one (disclosed in EP-A 294,666, Example 122, named "4-amino-1-(N-phenylcarbamoyl)-3-methyl-triazolin-5-one" in this publication.

Use Examples

In the Use Examples which follow, the compounds listed below were employed as comparison substances:

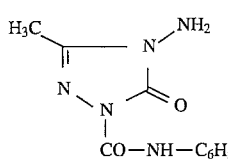

4-Amino-3-methyl-6-phenyl-1,2,4-triazin-5-one (disclosed in DE-OS (German Published Specification) 2,364,474, Example I-22)

4-Amino-1-(N-phenylcarbamoyl)-3-methyl-triazolin-5-one (disclosed in EP-A 294,666, Example 122)

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

a) Seeds of the test plants are sown in normal soil and, after 24 hours, watered with the preparation of active compound. It is expedient for this purpose to keep constant the amount of water per unit area. The concentration of active compound in the preparation is of no importance, only the application rate of the active compound per unit area being decisive. After three weeks, the degree of damage to the plants is rated in % damage in comparison to the development of the untreated control. The figures denote:

0%=no action (like untreated control)

100%=total destruction

A clearly superior effectiveness in the control of dicotyledon weeds compared with comparison substance (A) is shown in this test, for example, by the compounds of Preparation Examples (3), (5) and (6).

b) Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, a clearly superior herbicidal activity compared with comparison substance (A) is shown, for example, by the compounds according to Preparation Examples: (1), (3) and (4).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)

100%=total destruction

A clearly superior effectiveness in the control of dicotyledon weeds compared with comparison substances (A) and (B) is shown in this test, for example, by the compounds of Preparation Examples (3), (5) and (6).

Example C

Erysiphe Test (barley)/curative

Solvent: 100 parts by weight dimethylformamide

Emulsifier: 0.25 parts by weight alkylarylpolyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp.hordei. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

In this test, an excellent activity is shown, for example, by the compounds according to the following preparation examples: 9, 12, 15, 22 and 24.

Example D

Erysiphe Test (wheat)/curative

Solvent: 100 parts by weight dimethylformamide

Emulsifier: 0.25 parts by weight alkylarylpolyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp.hordei. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

In this test, an excellent activity is shown, for example, by the compounds according to the following preparation examples: 9, 10, 12, 15, 22, 23 and 24.

It will be understood that the specification and examples are illustrative but not limitative of the present invention and that other embodiments within the spirit and scope of the invention will suggest themselves to those skilled in the art.

We claim:

1. A substituted triazolinone of the formula

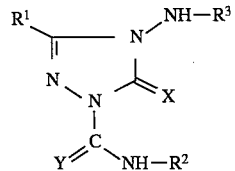

(I)

in which $R^1$ represents H, $C_1$–$C_4$-alkyl or cyclopropyl, $R^2$ represents $C_{1-8}$-alkyl, $C_{2-8}$-alkenyl or alkinyl, halo-$C_{1-8}$-alkyl, optionally $C_{1-4}$-alkyl substituted $C_{3-8}$-cycloalkyl, phenoxy-$C_{1-4}$-alkyl, cyano-$C_{1-8}$-alkyl, phenyl-$C_{1-6}$-alkyl (optionally substituted by halogen, $C_{1-4}$-haloalkoxy, $C_{1-4}$-alkoxy or $C_{1-4}$-alkyl), $C_{3-6}$-cycloalkyl-$C_{1-4}$-alkyl, or phenyl-$C_{2-5}$-alkinyl (optionally substituted by $C_{1-4}$-haloalkoxy);

$R^3$ represents $C_{1-8}$-alkyl;

X represents oxygen or sulfur; and

Y represents oxygen or sulfur.

2. A compound according to claim 1, in which $R^1$ represents H or $C_{1-4}$-alkyl, and $R^2$ represents $C_{1-8}$-alkyl, $C_{2-8}$-alkenyl or alkinyl, halo-$C_{1-8}$-alkyl, optionally methyl or ethyl substituted $C_{3-8}$-cycloalkyl,, or phenyl-$C_{1-4}$-alkyl.

3. A compound according to claim 1, wherein such compound is 1-[N-(1,1-dimethyl-ethyl)-carbamoyl]-3-methyl-4-methylamino-1,2,4-triazolin-5-one of the formula

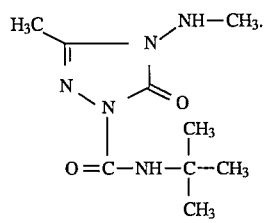

4. A compound according to claim 1, wherein such compound is 1-[N-(1,1-dimethyl-ethyl)-carbamoyl]-3-isopropyl-4-methylamino-1,2,4-triazolin-5-one of the formula

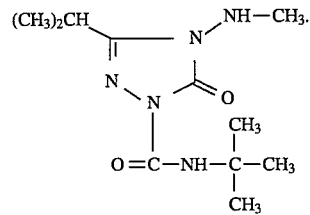

5. A compound according to claim 1, wherein such compound is 1-[N-(1-chloromethyl-1-methyl-ethyl)-carbamoyl]-3-isopropyl-4-methylamino-1,2,4-triazolin-5-one of the formula

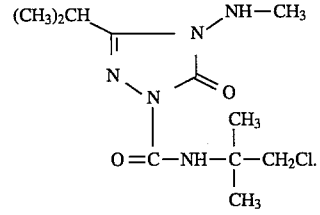

6. A compound according to claim 1, wherein such compound is

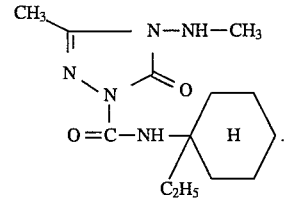

7. A compound according to claim 1, wherein such compound is

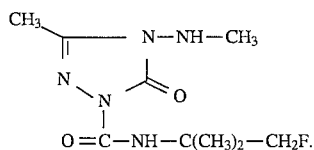

8. A compound according to claim 1, wherein such compound is

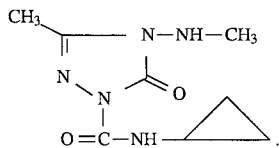

9. A compound according to claim 1, wherein such compound is

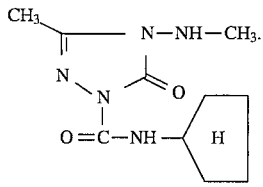

10. A compound according to claim 1, wherein such compound is

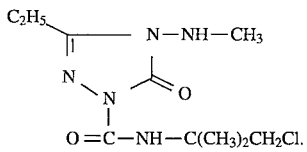

11. A compound according to claim 1, wherein such compound is

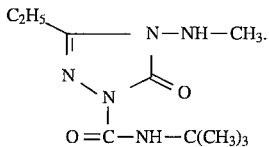

12. A compound according to claim 1, wherein such compound is

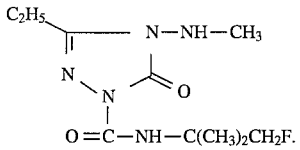

13. A compound according to claim 1, wherein such compound is 1-(N-t-butyl-carbamoyl)-3-cyclopropyl-4-methylamino-1,2,4-triazolin-5-one of the formula

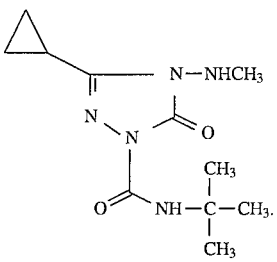

14. A compound according to claim 1, wherein such compound is 1-[N-methyl-cyclopentyl)-carbamoyl]-3-cyclopropyl-4-methylamino-1,2,4-triazol-5-one of the formula

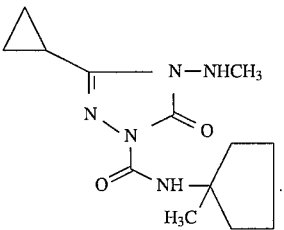

15. A compound according to claim 1, wherein such compound is 1-[N-(1,1-dimethyl-prop-2-inyl)-carbamoyl]-3-cyclopropyl-4-methylamino-1,2,4-triazolin-5-one of the formula

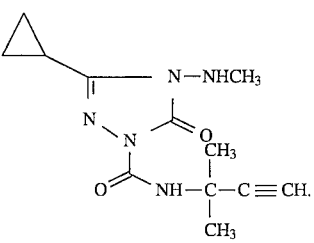

16. A compound according to claim 1, wherein such compound is 1-[N-isopropyl-carbamoyl)]-3-cyclopropyl-4-methylamino-1,2,4-triazolin-5-one of the formula

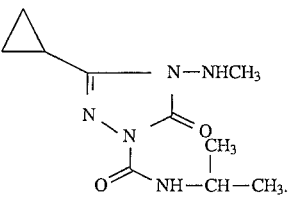

17. A compound according to claim 1, wherein such compound is 1-[N-(1,2-dimethyl-propyl)-carbamoyl]-3-cyclopropyl-4-methylamino-1,2,4- triazolin-5-one of the formula

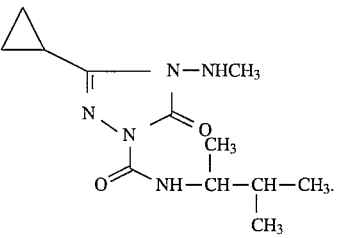

18. A compound according to claim 1, wherein such compound is 1-[N-(N-sec-butyl-carbamoyl)]-3-cyclopropyl 4-methylamino-1,2,4-triazolin-5-one of the formula

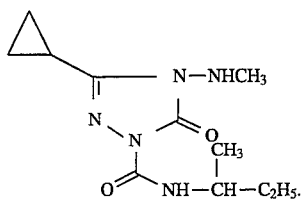

19. A compound according to claim 1, wherein such compound is 1-[N-(1-cyano-1-methyl-ethyl)]-carbamoyl]-3-cyclopropyl-4-methylamino-1,2,4-triazolin-5-one of the formula

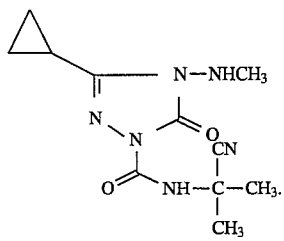

20. A compound according to claim 1, wherein such compound is 2-(1,1-dimethyl-3-(4-trifluoromethoxyphenyl)propylaminocarbonyl)-5-methyl-4-methylamino-2,4-dihydro-3H-1,2,4-triazol-3-one

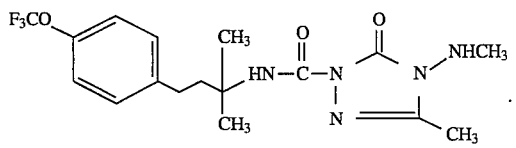

21. A compound according to claim 1, wherein such compound is 2-(1,1-dimethyl-3-(4-methoxyphenyl)propylaminocarbonyl)-4-methylamino-5-methyl-2,4-dihydro-3H-1,2,4-triazol-3-one

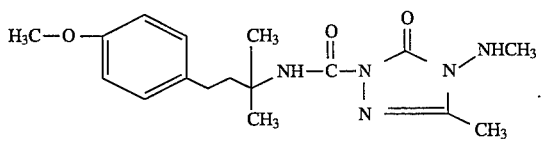

22. A compound according to claim 1, wherein such compound is 2-(1-methyl-3-(4-chlorophenyl)propylaminocarbonyl)-4-methylamino-5-methyl-2,4-dihydro-3H-1,2,4-triazol-3-one

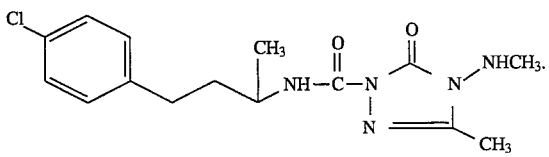

23. A compound according to claim 1, wherein such compound is 2-(1-methyl-3-(4-chlorophenyl)propylaminocarbonyl)-5-ethyl-4-methylamino-2,4-dihydro-3H-1,2,4-triazol-3-one

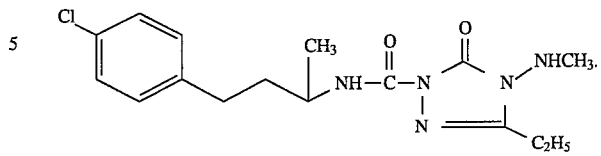

24. A compound according to claim 1, wherein such compound is 2-(1-methyl-3-(4-chlorophenyl)propylaminocarbonyl)-5-cyclopropyl-4-methylamino-2,4-dihydro-3H-1,2,4-triazol-3-one

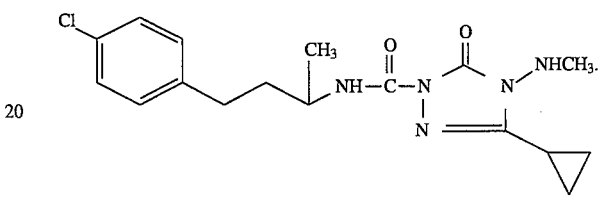

25. A compound according to claim 1, wherein such compound is 2-(1-methyl-3-(4-fluorophenyl)propylaminocarbonyl)-5-methyl-4-methylamino-2,4-dihydro-3H-1,2,4-triazol-3-one

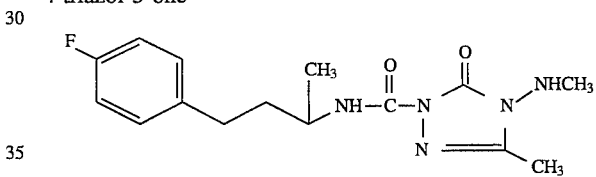

26. A compound according to claim 1, wherein such compound is 2-(1,2-dimethyl-3-(3,4-dimethylphenyl)propylamino-carbonyl)-5-methyl-4-methylamino-2,4-dihydro-3H-1,2,4-triazol-3-one of the formula

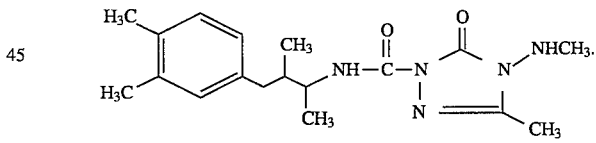

27. A herbicidal and fungicidal composition comprising a herbicidally or fungicidally effective amount of a compound according to claim 3 and a diluent.

28. A method of combating unwanted vegetation or fungi which comprises applying to such vegetation, fungi or to a locus from which it is desired to exclude such vegetation or fungi a or fungicidally herbicidally effective amount of a compound according to claim 1.

* * * * *

UNITED STATES PATENT AND TRADEMARK OFFICE
CERTIFICATE OF CORRECTION

PATENT NO. : 5,516,749
DATED      : May 14, 1996
INVENTOR(S): Muller, et al.

It is certified that error appears in the above-indentified patent and that said Letters Patent is hereby corrected as shown below:

Col. 78, line 52          Delete claim " 3 " and substitute claim -- 1 --

Col. 78, Next to last line    Delete " or fungicidally herbicidally " and substitute -- herbicidally or fungicidally --

Signed and Sealed this

Twenty-second Day of October, 1996

Attest:

BRUCE LEHMAN

Attesting Officer       Commissioner of Patents and Trademarks